United States Patent
Woo et al.

(10) Patent No.: US 10,155,964 B2
(45) Date of Patent: Dec. 18, 2018

(54) **TRANSFORMED *SYNECHOCOCCUS ELONGATUS* STRAIN HAVING CAPABILITY OF PRODUCING SQUALENE FROM CARBON DIOXIDE AND METHOD FOR PRODUCING SQUALENE USING THE SAME**

(71) Applicant: Korea Institute of Science and Technology, Seoul (KR)

(72) Inventors: Han Min Woo, Seoul (KR); Sun-young Choi, Seoul (KR); Youngsoon Um, Seoul (KR); Gyeong Taek Gong, Seoul (KR); Sun Mi Lee, Seoul (KR); Yunje Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 39 days.

(21) Appl. No.: 15/357,815

(22) Filed: Nov. 21, 2016

(65) Prior Publication Data
US 2017/0283832 A1    Oct. 5, 2017

(30) Foreign Application Priority Data
Apr. 5, 2016   (KR) .................. 10-2016-0041774

(51) Int. Cl.
*C12N 9/04* (2006.01)
*C12N 9/10* (2006.01)
*C12N 9/90* (2006.01)
*C12P 5/00* (2006.01)
*C12N 15/52* (2006.01)

(52) U.S. Cl.
CPC ............ *C12P 5/007* (2013.01); *C12N 9/0006* (2013.01); *C12N 9/1022* (2013.01); *C12N 9/1085* (2013.01); *C12N 9/90* (2013.01); *C12N 15/52* (2013.01); *C12Y 101/01267* (2013.01); *C12Y 202/01007* (2013.01); *C12Y 205/0101* (2013.01); *C12Y 205/01021* (2013.01); *C12Y 503/03002* (2013.01)

(58) Field of Classification Search
CPC .......... C12P 23/00; C12P 5/002; C12P 7/065; C12N 15/52; C12N 15/70; C12N 1/20; C12N 9/90; C12Y 101/01034; C12Y 402/03027; C12Y 202/01007
See application file for complete search history.

(56) References Cited

U.S. PATENT DOCUMENTS
7,098,000 B2   8/2006   Cheng et al.
2004/0015033 A1   1/2004   Steiner et al.

FOREIGN PATENT DOCUMENTS
JP                5-90 A       1/1993
KR   10-2003-0036246 A         5/2003

OTHER PUBLICATIONS

Heterologous Expression of the Mevalonic Acid Pathway in Cyanobacteria Enhances Endogenous Carbon Partitioning to Isoprene Fiona K. Bentley. Molecular Plant vol. 7 No. 1 pp. 71-86 Jan. 2014. (Year: 2014).*
Synechococcus elongatus UTEX 2973, a fast growing cyanobacterial chassis for biosynthesis using light and CO2 Jingjie Yu. PLOS ONE Mar. 1, 2014 vol. 9 Issue 3 (Year: 2014).*
Production of Squalene in Synechocystis sp. PCC 6803 Elias Englund1 Scientific Reports 5 : 8132 | (Year: 2014).*
Engineering a platform for photosynthetic isoprene production in cyanobacteria, using Synechocystis as the model organism Pia Lindberg Metabolic Engineering 12 (2010) 70-79 (Year: 2010).*
Bhattacharjee, P., et al. "Studies on Fermentative Production of Squalene." *World Journal of Microbiology and Biotechnology* 17.8 (2001): 811-816. (6 pages, in English).
Englund, Elias, et al. "Production of Squalene in Synechocystis sp. PCC 6803." *PloS one* 9.3 (2014): e90270. (8 pages, in English).
Kim, Seon-Won, and J. D. Keasling. "Metabolic Engineering of the Nonmevalonate Isopentenyl Diphosphate Synthesis Pathway in *Escherichia coli* Enhances Lycopene Production." *Biotechnology and Bioengineering* 72.4 (2001): 408-415. (8 pages, in English).
Lee, Taek Soon, et al. "Bglbrick Vectors and Datasheets: A Synthetic Biology Platform for Gene Expression." Journal of Biological Engineering 5.1 (2011): 1. (14 pages, in English).
Lan, Ethan I., et al. "Metabolic engineering of cyanobacteria for 1-butanol production from carbon dioxide." *Metabolic engineering* 13.4 (2011): 353-363. (11 pages, in English).

* cited by examiner

Primary Examiner — Kagnew H Gebreyesus
(74) Attorney, Agent, or Firm — NSIP Law

(57) ABSTRACT

The present specification discloses a transformed *Synechococcus elongatus* strain which may directly produce squalene from carbon dioxide, and a method for producing squalene and a method for removing carbon dioxide, using the same. In an aspect, the strain may produce squalene using carbon dioxide as a carbon source. The *Synechococcus elongatus* strain is economically efficient because a high-value added squalene is produced using light and carbon dioxide present in the atmosphere as a carbon source, and the method for producing squalene is eco-friendly because the strain may be utilized to remove or reduce carbon dioxide in the atmosphere by using microorganisms. The strain of the present disclosure may produce only squalene, which is a desired target material with high purity, and has an advantage in that squalene may be continuously mass-produced.

11 Claims, 7 Drawing Sheets

Specification includes a Sequence Listing.

SEQUENCE LISTING

```
<160> NUMBER OF SEQ ID NOS: 14

<210> SEQ ID NO 1
<211> LENGTH: 1863
<212> TYPE: DNA
<213> ORGANISM: Artificial Sequence
<220> FEATURE:
<223> OTHER INFORMATION: dxs gene

<400> SEQUENCE: 1
atgagctttg atatcgccaa atacccacc  ctggccctgg tggatagcac ccaggaactg      60
cgcctgctgc ccaaagaaag cctgcccaaa ctgtgcgatg aactgcgccg ctacctgctg     120
gatagcgtga gccgcagcag cggccacttt gccagcggcc tgggcaccgt ggaactgacc     180
gtggccctgc actacgtgta caacaccccc tttgatcagc tgatctggga tgtgggccac     240
caggcctacc cccacaaaat cctgaccggc cgccgcgata aaatcggcac catccgccag     300
aaaggcggcc tgcacccctt tccctggcgc ggcgaaagcg aatacgatgt gctgagcgtg     360
ggccacagca gcaccagcat cagcgccggc atcggcatcg ccgtggccgc cgaaaaagaa     420
ggcaaaaacc gccgcaccgt gtgcgtgatc ggcgatggcg ccatcaccgc cggcatggcc     480
tttgaagcca tgaaccacgc cggcgatatc cgccccgata tgctggtgat cctgaacgat     540
aacgaaatga gcatcagcga aaacgtgggc gccctgaaca accacctggc ccagctgctg     600
agcggcaaac tgtacagcag cctgcgcgaa ggcggcaaaa aagtgtttag cggcgtgccc     660
cccatcaaag aactgctgaa acgcaccgaa gaacacatca aaggcatggt ggtgcccggc     720
accctgtttg aagaactggg ctttaactac atcggccccg tggatggcca cgatgtgctg     780
```

```
ggcctgatca ccaccctgaa aaacatgcgc gatctgaaag gcccccagtt cctgcatatc      840
atgaccaaaa aaggccgcgg ctacgaaccc gccgaaaaag atcccatcac ctttcacgcc      900
gtgcccaaat ttgatcccag cagcggctgc ctgcccaaaa gcagcggcgg cctgcccagc      960
tacagcaaaa tctttggcga ttggctgtgc gaaaccgccg ccaaagataa caaactgatg     1020
gccatcaccc ccgccatgcg cgaaggcagc ggcatggtgg aatttagccg caaatttccc     1080
gatcgctact tgatgtggc catcgccgaa cagcacgccg tgacctttgc cgccggcctg      1140
gccatcggcg gctacaaacc catcgtggcc atctacagca cctttctgca gcgcgcctac     1200
gatcaggtgc tgcacgatgt ggccatccag aaactgcccg tgctgtttgc catcgatcgc     1260
gccggcatcg tgggcgccga tggccagacc caccagggcg cctttgatct gagctacctg     1320
cgctgcatcc ccgaaatggt gatcatgacc cccagcgatg aaaacgaatg ccgccagatg     1380
ctgtacaccg gctaccacta caacgatggc cccagcgccg tgcgctaccc ccgcggcaac     1440
gccgtgggcg tggaactgac cccccctggaa aaactgccca tcggcaaagg catcgtgaaa     1500
cgccgcggcg aaaaactggc catcctgaac tttggcaccc tgatgcccga agccgccaaa     1560
gtggccgaaa gcctgaacgc caccctggtg gatatgcgct tgtgaaacc cctggatgaa      1620 gccctgatcc tggaaatggc cgccagccac gaagccctgg tgaccgtgga agaaaacgcc     1680
atcatgggcg cgccggcag cggcgtgaac gaagtgctga tggcccaccg caaacccgtg     1740
cccgtgctga acatcggcct gccgatttt tttatccccc agggcaccca ggaagaaatg      1800
cgcgccgaac tgggcctgga tgccgccggc atggaagcca aaatcaaagc ctggctggcc     1860
tag                                                                   1863

<210> SEQ ID NO 2
<211> LENGTH: 549
<212> TYPE: DNA
<213> ORGANISM: Artificial Sequence
<220> FEATURE:
<223> OTHER INFORMATION: idi gene

<400> SEQUENCE: 2
atgcagaccg aacacgtgat cctgctgaac gcccagggcg tgccaccgg caccctggaa       60 aaatacgccg cccacaccgc cgataccccgc ctgcacctgg cctttagcag ctggctgttt     120
aacgccaaag gccagctgct ggtgaccccgc cgcgccctga gcaaaaaagc ctggcccggc     180
gtgtggacca cagcgtgtg cggccacccc cagctgggcg aaagcaacga agatgccgtg      240
atccgccgct gccgctacga actgggcgtg gaaatcaccc ccccgaaag catctacccc     300 gattttcgct accgcgccac cgatcccagc ggcatcgtgg aaaacgaagt gtgccccgtg     360
tttgccgccc gcaccaccag cgccctgcag atcaacgatg atgaagtgat ggattaccag     420
tggtgcgatc tggccgatgt gctgcacggc atcgatgcca cccccctggg cctttagcccc     480 tggatggtga tgcaggccac caaccgcgaa gcccgcaaac gcctgagcgc ctttacccag      540
ctgaaatag                                                              549

<210> SEQ ID NO 3
<211> LENGTH: 900
<212> TYPE: DNA
<213> ORGANISM: Artificial Sequence
<220> FEATURE:
<223> OTHER INFORMATION: ispA gene

<400> SEQUENCE: 3
```

| | |
|---|---|
| atggattttc cccagcagct ggaagcctgc gtgaaacagg ccaaccaggc cctgagccgc | 60 |
| tttatcgccc ccctgccctt tcagaacacc cccgtggtgg aaaccatgca gtacggcgcc | 120 |
| ctgctgggcg gcaaacgcct gcgccccttt ctggtgtacg ccaccggcca catgtttggc | 180 |
| gtgagcacca caccctgga tgccccgcc gccgcgtgg aatgcatcca cgcctacagc | 240 |
| ctgatccacg atgatctgcc cgccatggat gatgatgatc tgcgccgcgg cctgcccacc | 300 |
| tgccacgtga atttggcga agccaacgcc atcctggccg gcgatgccct gcagaccctg | 360 |
| gcctttagca tcctgagcga tgccgatatg cccgaagtga gcgatcgcga tcgcatcagc | 420 |
| atgatcagcg aactggccag cgccagcggc atcgccggca tgtgcggcgg ccaggccctg | 480 |
| gatctggatg ccgaaggcaa acacgtgccc ctggatgccc tggaacgcat ccaccgccac | 540 |
| aaaaccggcg ccctgatccg cgccgccgtg cgcctgggcg ccctgagcgc cggcgataaa | 600 |
| ggccgccgcg ccctgcccgt gctggataaa tacgccgaaa gcatcggcct ggcctttcag | 660 |
| gtgcaggatg atatcctgga tgtggtgggc gataccgcca ccctgggcaa acgccagggc | 720 |
| gccgatcagc agctgggcaa aagcacctac cccgccctgc tgggcctgga acaggcccgc | 780 |
| aaaaaagccc gcgatctgat cgatgatgcc cgccagagcc tgaaacagct ggccgaacag | 840 |
| agcctggata ccagcgccct ggaagccctg gccgattaca tcatccagcg caacaaatag | 900 |

<210> SEQ ID NO 4
<211> LENGTH: 1263
<212> TYPE: DNA
<213> ORGANISM: Artificial Sequence
<220> FEATURE:
<223> OTHER INFORMATION: sqs gene derived from Saccharomyces cerevisiae

<400> SEQUENCE: 4

| | |
|---|---|
| atgggcaaac tgctgcagct ggccctgcac cccgtggaaa tgaaagccgc cctgaaactg | 60 |
| aaattttgcc gcacccccct gtttagcatc tacgatcaga gcaccagccc ctacctgctg | 120 |
| cactgctttg aactgctgaa cctgaccagc cgcagctttg ccgccgtgat ccgcgaactg | 180 |
| caccccgaac tgcgcaactg cgtgaccctg tttacctga tcctgcgcgc cctggatacc | 240 |
| atcgaagatg atatgagcat cgaacacgat ctgaaaatcg atctgctgcg ccactttcac | 300 |
| gaaaaactgc tgctgaccaa atggagcttt gatggcaacg cccccgatgt gaaagatcgc | 360 |
| gccgtgctga ccgattttga agcatcctg atcgaatttc acaaactgaa acccgaatac | 420 |
| caggaagtga tcaaagaaat caccgaaaaa atgggcaacg gcatggccga ttacatcctg | 480 |
| gatgaaaact acaacctgaa cggcctgcag accgtgcacg attacgatgt gtactgccac | 540 |
| tacgtggccg gcctggtggg cgatggcctg accgcctga tcgtgatcgc caaatttgcc | 600 |
| aacgaaagcc tgtacagcaa cgaacagctg tacgaaagca tgggcctgtt tctgcagaaa | 660 |
| accaacatca tccgcgatta caacgaggat ctggtggatg ccgcagctt ttggcccaaa | 720 |
| gaaatctgga ccagtacgc ccccagctg aaagattta tgaaacccga aaacgaacag | 780 |
| ctgggcctgg attgcatcaa ccacctggtg ctgaacgccc tgagccacgt gatcgatgtg | 840 |
| ctgacctacc tggccggcat ccacgaacag agcacctttc agтттгgcgc catccccag | 900 |
| gtgatggcca tcgccaccct ggccctggtg tttaacaacc gcgaagtgct gcacggcaac | 960 |
| gtgaaaatcc gcaaaggcac cacctgctac ctgatcctga aagccgcac cctgcgcggc | 1020 |
| tgcgtggaaa тсттгgatта ctacctgcgc gatatcaaaa gcaaactggc cgtgcaagat | 1080 |
| cccaactttc tgaaactgaa catccagatc agcaaaatcg aacagtttat ggaagaaatg | 1140 |
| taccaggata aactgccccc caacgtgaaa cccaacgaaa ccccccatct ттctgaaagtg | 1200 |

| | |
|---|---|
| aaagaacgca gccgctacga tgatgaactg gtgcccaccc agcaggaaga agaatacaaa | 1260 |
| tag | 1263 |

<210> SEQ ID NO 5
<211> LENGTH: 1089
<212> TYPE: DNA
<213> ORGANISM: Artificial Sequence
<220> FEATURE:
<223> OTHER INFORMATION: sqs gene derived from Methylococcus capsulatus

<400> SEQUENCE: 5

| | |
|---|---|
| atgagcggca cccccccag ccagcccgcc cgccacgaac acctgagcga tgatgaattt | 60 |
| caggcccact ttctggatgg cgtgagccgc acctttgccc tgaccatccc ccgcctgccc | 120 |
| gaaggcctgg cccgccccgt gagcaacggc tacctgctgt gccgcatcgt ggataccatc | 180 |
| gaagatgaag tggccctgac cagcacccag aaacgccgct actgcgaaca ctttgcccgc | 240 |
| gtggtggccg gcaccgcccc cgccgccccc ctggccgatg aactgttcc cctgctgagc | 300 |
| gatcagaccc tggccgccga acgcgaactg atcgccgcca tccccgcgt gatcagcatc | 360 |
| acccacggct tgccgcccc ccagcaggaa gccctggccg aatgcgtggc caccatgagc | 420 |
| cgcggcatgg ccgaatttca ggataaggat ctgcgccacg gcctggagga tctgcgccag | 480 |
| atgggcgatt actgctacta cgtggccggc gtggtgggcg aaatgctgac ccgcctgttt | 540 |
| tgccactaca gccccgaaat cgccgcccac cgcagccgcc tgatggaact ggcctgcccc | 600 |
| tttggccagg cctgcagat gaccaacatc ctgaaggatc tgtgggatga tcacgcccgc | 660 |
| ggcgtgtgct ggctgcccca ggaagtgttt accgaatgcg gctttagcct gaccgaactg | 720 |
| cgccccccacc acgccaaccc cgattttgtg cgcggctttg aacgcctgat cggcgtggcc | 780 |
| cacgccacc tgcgcaacgc cctggaatac accctgctga tccccgcca cgaaaccggc | 840 |
| atccgcgaat tttgcctgtg ggccctgggc atggccgtgc tgaccctgcg caaaatccac | 900 |
| cgccacccct actttagcga tagcgcccag gtgaaaatca cccgccaggc cgtgaaagcc | 960 |
| accatcgtga ccagccgcct gaccgcgcgc agcgatcccc tgctgaaagc caccttcgc | 1020 |
| ctggccggcc tgggcctgcc cgccgccgtg cccgccgccg tgctgcagcc ccgccccatc | 1080 |
| gatatctag | 1089 |

<210> SEQ ID NO 6
<211> LENGTH: 1197
<212> TYPE: DNA
<213> ORGANISM: Artificial Sequence
<220> FEATURE:
<223> OTHER INFORMATION: dxr gene

<400> SEQUENCE: 6

| | |
|---|---|
| atgaaacagc tgaccatcct gggcagcacc ggcagcatcg gctgcagcac cctggatgtg | 60 |
| gtgcgccaca ccccgaaca cttccgcgtg gtgcccctgg tggccggcaa aaacgtgacc | 120 |
| cgcatggtgg aacagtgcct ggaatttagc ccccgctacg ccgtgatgga tgatgaagcc | 180 |
| agcgccaaac tgctgaaaac catgctgcag cagcagggca gccgcaccga agtgctgagc | 240 |
| ggccagcagg ccgcctgcga tatggccgcc ctggaagatg tggatcaggt gatggccgcc | 300 |
| atcgtgggcg ccgccggcct gctgccccacc ctggccgcca tccgcgccgg caaaaccatc | 360 |
| ctgctggcca caaagaaag cctggtgacc tgcggccgcc tgtttatgga tgccgtgaaa | 420 |
| cagagcaaag cccagctgct gcccgtggat agcgaacaca acgccatctt tcagagcctg | 480 |

| | |
|---|---|
| ccccagccca tccagcacaa cctgggctac gccgatctgg aacagaacgg cgtggtgagc | 540 |
| atcctgctga ccggcagcgg cggcccctt cgcgaaaccc ccctgcgcga tctggccacc | 600 |
| atgacccccg atcaggcctg ccgccacccc aactggagca tgggccgcaa aatcagcgtg | 660 |
| gatagcgcca ccatgatgaa caaaggcctg gaatacatcg aagcccgctg gctgtttaac | 720 |
| gccagcgcca gccagatgga agtgctgatc caccccccaga gcgtgatcca cagcatggtg | 780 |
| cgctaccagg atggcagcgt gctggcccag ctgggcgaac ccgatatgcg cacccccatc | 840 |
| gcccacacca tggcctggcc caaccgcgtg aacagcggcg tgaaacccct ggattttgc | 900 |
| aaactgagcg ccctgacctt tgccgcccc gattacgatc gctacccctg cctgaaactg | 960 |
| gccatggaag cctttgaaca gggccaggcc gccaccaccg ccctgaacgc cgccaacgaa | 1020 |
| atcaccgtgg ccgcctttct ggcccagcag atccgcttta ccgatatcgc cgccctgaac | 1080 |
| ctgagcgtgc tggaaaaaat ggatatgcgc gaaccccagt gcgtggatga tgtgctgagc | 1140 |
| gtggatgcca acgccgcga agtggcccgc aaagaagtga tgcgcctggc cagctag | 1197 |

<210> SEQ ID NO 7
<211> LENGTH: 8790
<212> TYPE: DNA
<213> ORGANISM: Artificial Sequence
<220> FEATURE:
<223> OTHER INFORMATION: pSe1Bb1s-dxs-idi-ispA vector

<400> SEQUENCE: 7

| | |
|---|---|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| cttttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |
| tcaagacgat agttaccgga taaggcgcag cggtcgggct gaacgggggg ttcgtgcaca | 420 |
| cagcccagct tggagcgaac gacctacacc gaactgagat acctacagcg tgagctatga | 480 |
| gaaagcgcca cgcttcccga agggagaaag gcggacaggt atccggtaag cggcagggtc | 540 |
| ggaacaggag agcgcacgag ggagcttcca ggggaaacg cctggtatct ttatagtcct | 600 |
| gtcgggtttc gccacctctg acttgagcgt cgatttttgt gatgctcgtc aggggggcgg | 660 |
| agcctatgga aaaacgccag caacgcggcc ttttacggt tcctggcctt ttgctggcct | 720 |
| tttgctcaca tgtgtgctgg gccccaatgc cttctccaag ggcggcattc ccctgactgt | 780 |
| tgaaggcgtt gccaatatca agattgctgg ggaagaaccg accatccaca acgcgatcga | 840 |
| gcggctgctt ggcaaaaacc gtaaggaaat cgagcaaatt gccaaggaga ccctcgaagg | 900 |
| caacttgcgt ggtgttttag ccagcctcac gccggagcag atcaacgagg acaaaattgc | 960 |
| ctttgccaaa agtctgctgg aagaggcgga ggatgacctt gagcagctgg gtcaagtcct | 1020 |
| cgatacgctg caagtccaga acatttccga tgaggtcggt tatctctcgg ctagtggacg | 1080 |
| caagcagcgg gctgatctgc agcgagatgc ccgaattgct gaagccgatg cccaggctgc | 1140 |
| ctctgcgatc caaacggccg aaaatgacaa gatcacggcc ctgcgtcgga tcgatcgcga | 1200 |
| tgtagcgatc gcccaagccg aggccgagcc ccggattcag gatgcgttga gcggcgcga | 1260 |
| agcggtggtg gccgaagctg aagcggacat tgctaccgaa gtcgctcgta gccaagcaga | 1320 |
| actccctgtg cagcaggagc ggatcaaaca ggtgcagcag caacttcaag ccgatgtgat | 1380 |

```
cgccccagct gaggcagctt gtaaacgggc gatcgcggaa gcgcgggggg ccgccgcccg    1440
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga gcggtgatc    1920 gccgaagtat cgactcaact atcagaggta gttggcgtca tcgagcgcca tctcgaaccg    1980
acgttgctgg ccgtacattt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact cttttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aacctttcgc ggtatggcat    2760
gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca atcgcgctg ttagcgggcc    3360 cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
```

```
ctcagggcca ggcggtgaag ggcaatcagc tgttgcccgt ctcactggtg aaagaaaaa      3780
ccaccctggc gcccaatacg caaaccgcct ctccccgcgc gttggccgat tcattaatgc      3840
agctggcacg acaggtttcc cgactggaaa gcgggcagtg agcgcaacgc aattaatgta      3900
agttagcgcg aattgatctg gtttgacagc ttatcatcga ctgcacggtg caccaatgct      3960
tctggcgtca ggcagccatc ggaagctgtg gtatggctgt gcaggtcgta atcactgca      4020
taattcgtgt cgctcaaggc gcactcccgt tctggataat gttttttgcg ccgacatcat      4080
aacggttctg gcaaatattc tgaaatgagc tgttgacaat taatcatccg gctcgtataa      4140
tgtgtggaat tgtgagcgga taacaatttc agaattcaaa agatctaaag aggagaaata      4200
ctagatgagc tttgatatcg ccaaataccc caccctggcc ctggtggata gcacccagga      4260
actgcgcctg ctgcccaaag aaagcctgcc caaactgtgc gatgaactgc gccgctacct      4320
gctggatagc gtgagccgca gcagcggcca ctttgccagc ggcctgggca ccgtggaact      4380
gaccgtggcc ctgcactacg tgtacaacac ccccttgat cagctgatct gggatgtggg      4440
ccaccaggcc taccccaca aaatcctgac cggccgccgc gataaaatcg gcaccatccg      4500
ccagaaaggc ggcctgcacc cctttccctg cgcggcgaa agcgaatacg atgtgctgag      4560
cgtgggccac agcagcacca gcatcagcgc cggcatcgga atcgccgtgg ccgccgaaaa      4620
agaaggcaaa aaccgccgca ccgtgtgcgt gatcggcgat ggcgccatca ccgccggcat      4680
ggcctttgaa gccatgaacc acgcggcga tatccgcccc gatatgctgg tgatcctgaa      4740
cgataacgaa atgagcatca gcgaaaacgt gggcgccctg aacaaccacc tggcccagct      4800
gctgagcgga aaactgtaca gcagcctgcg cgaaggcgcg aaaaaagtgt ttagcggcgt      4860
gcccccatc aaagaactgc tgaaacgcac cgaagaacac atcaaaggca tggtggtgcc      4920
cggcaccctg tttgaagaac tgggctttaa ctacatcggc cccgtggatg ccacgatgt      4980
gctgggcctg atcaccaccc tgaaaaacat gcgcgatctg aaaggccccc agttcctgca      5040
tatcatgacc aaaaaaggcc gcggctacga accgccgaa aaagatccca tcaccttttca      5100
cgccgtgccc aaatttgatc cagcagcgg ctgcctgccc aaaagcagcg gcggcctgcc      5160
cagctacagc aaaatctttg gcgattggct gtgcgaaacc gccgccaaag ataacaaact      5220
gatggccatc accccccgcca tgcgcgaagg cagcggcatg gtggaattta ccgcaaatt      5280
tcccgatcgc tactttgatg tggccatcgc cgaacagcac gccgtgacct ttgccgccgg      5340
cctggccatc ggcggctaca acccatcgt ggccatctac agcaccttc tgcagcgcgc      5400
ctacgatcag gtgctgcacg atgtggccat ccagaaactg cccgtgctgt ttgccatcga      5460
tcgcgccggc atcgtgggcg ccgatggcca gaccaccag ggcgccttg atctgagcta      5520
cctgcgctgc atccccgaaa tggtgatcat gaccccagc gatgaaaacg aatgccgcca      5580
gatgctgtac accggctacc actacaacga tggccccagc gccgtgcgct accccgcgg      5640
caacgccgtg ggcgtggaac tgaccccgt gaacttcccg atcgcagctg agtcgtccct      5700
cccccaacgg aaagctgaac atctccaact ctgtcttgag gctggagtcg aaagcccga      5760
ggtgacgacc gggttggagc gctatcgttt ccagcattgt gcgctgccaa atttgagtct      5820
gcaggcgctg gacctaggga cgcagttctt ggggcgatcg ctggggcac cgctgctgat      5880
ctcgtcgatg accggcggaa ccgaaaccct ggaaaaactg ccatcggca aggcatcgt      5940
gaaacgccgc ggcgaaaaac tggccatcct gaactttgcc accctgatgc ccgaagccgc      6000
caaagtggcc gaaagcctga acgccaccct ggtggatatg cgctttgtga aacccctgga      6060
tgaagccctg atcctggaaa tggccgccag ccacgaagcc ctggtgaccg tggaagaaaa      6120
```

```
cgccatcatg ggcggcgccg gcagcggcgt gaacgaagtg ctgatggccc accgcaaacc   6180
cgtgcccgtg ctgaacatcg gcctgcccga ttttttatc ccccagggca cccaggaaga    6240
aatgcgcgcc gaactgggcc tggatgccgc cggcatggaa gccaaaatca aagcctggct   6300
ggcctaggga tctaaagagg agaaatacta gatgcagacc gaacacgtga tcctgctgaa   6360
cgcccagggc gtgcccaccg gcaccctgga aaaatacgcc gcccacaccg ccgatacccg   6420
cctgcacctg gcctttagca gctggctgtt taacgccaaa ggccagctgc tggtgacccg   6480
ccgcgccctg agcaaaaaag cctggcccgg cgtgtggacc aacagcgtgt gcggccaccc   6540
ccagctgggc gaaagcaacg aagatgccgt gatccgccgc tgccgctacg aactgggcgt   6600
ggaaatcacc ccccccgaaa gcatctaccc cgattttcgc taccgcgcca ccgatcccag   6660
cggcatcgtg gaaaacgaag tgtgcccgt gtttgccgcc gcaccacca gcgcctgca    6720 gatcaacgat gatgaagtga tggattacca gtggtgcgat ctggccgatg tgctgcacgg   6780
catcgatgcc accccctggg cctttagccc ctggatggtg atgcaggcca ccaaccgcga   6840
agcccgcaaa cgcctgagcg cctttaccca gctgaaatag ggatctatta agaggagaa    6900 tactagatgg attttccca gcagctgaa gcctgcgtga acaggccaa ccaggccctg      6960 agccgcttta tcgccccct gccctttcag aacaccccg tggtggaaac catgcagtac     7020
ggcgccctgc tgggcggcaa acgctgcgc cccttctgg tgtacgccac cggccacatg     7080
tttggcgtga gcaccaacac cctggatgcc cccgccgccg ccgtggaatg catccacgcc   7140
tacagcctga tccacgatga tctgcccgcc atggatgatg atgatctgcg ccgcggcctg   7200
cccacctgcc acgtgaaatt tggcgaagcc aacgccatcc tggccggcga tgccctgcag   7260
accctggcct ttagcatcct gagcgatgcc gatatgcccg aagtgagcga tcgcgatcgc   7320
atcagcatga tcagcgaact ggccagcgcc agcggcatcc ccggcatgtg cggcggccag   7380
gccctggatc tggatgccga aggcaaacac gtgcccctgg atgccctgga acgcatccac   7440
cgccacaaaa ccggcgccct gatccgcgcc gccgtgcgcc tgggcgccct gagcgccggc   7500
gataaaggcc gccgcgccct gcccgtgctg gataaatacg ccgaaagcat cggcctggcc   7560
tttcaggtgc aggatgatat cctggatgtg gtgggcgata ccgccaccct gggcaaacgc   7620
cagggcgccg atcagcagct gggcaaaagc acctaccccg ccctgctggg cctggaacag   7680
gcccgcaaaa aagcccgcga tctgatcgat gatgcccgcc agagcctgaa acagctggcc   7740
gaacagagcc tggataccag cgccctggaa gccctggccg attacatcat ccagcgcaac   7800
aaatagggat ccaaactcga gtaaggatct ccaggcatca aataaaacga aaggctcagt   7860
cgaaagactg ggcctttcgt tttatctgtt gtttgtcggt gaacgctctc tactagagtc   7920
acactggctc accttcgggt gggcctttct gcgtttatac ctagggcgtt cggctgcggc   7980
gagcggtatc agctcactca aaggcggtaa tacgtccctg ctcgtcacgc tttcaggcac   8040
cgtgccagat atcgacgtgg agtcgatcac tgtgattggc gaaggggaag gcagcgctac   8100
ccaaatcgct agcttgctgg agaagctgaa acaaaccacg gcattgatc tggcgaaatc   8160 cctaccgggt caatccgact cgccgcgctg gaagtcctaa gagatagcga tgtgaccgcg   8220
atcgcttgtc aagaatccca gtgatcccga accataggaa ggcaagctca atgcttgcct   8280
cgtcttgagg actatctaga tgtctgtgga acgcacattt attgccatca gcccgatgg    8340 cgttcagcgg ggtttggtcg gtacgatcat cggccgcttt gagcaaaaag gcttcaaact   8400
ggtgggccta aagcagctga agcccagtcg cgagctggcc gaacagcact atgctgtcca   8460
```

```
ccgcgagcgc cccttcttca atggcctcgt cgagttcatc acctctgggc cgatcgtggc    8520
gatcgtcttg gaaggcgaag gcgttgtggc ggctgctcgc aagttgatcg gcgctaccaa    8580
tccgctgacg gcagaaccgg gcaccatccg tggtgatttt ggtgtcaata ttggccgcaa    8640
catcatccat ggctcggatg caatcgaaac agcacaacag gaaattgctc tctggtttag    8700
cccagcagag ctaagtgatt ggaccccac gattcaaccc tggctgtacg aataaggtct     8760
gcattccttc agagagacat tgccatgccg                                     8790

<210> SEQ ID NO 8
<211> LENGTH: 9773
<212> TYPE: DNA
<213> ORGANISM: Artificial Sequence
<220> FEATURE:
<223> OTHER INFORMATION: pSe1Bb1s-dxs-dxr-idi-ispA vector

<400> SEQUENCE: 8
gataatctca tgaccaaaat cccttaacgt gagttttcgt tccactgagc gtcagacccc      60
gtagaaaaga tcaaaggatc ttcttgagat cctttttttc tgcgcgtaat ctgctgcttg     120
caaacaaaaa aaccaccgct accagcggtg gtttgtttgc cggatcaaga gctaccaact     180
cttttttccga aggtaactgg cttcagcaga gcgcagatac caaatactgt tcttctagtg     240
tagccgtagt taggccacca cttcaagaac tctgtagcac cgcctacata cctcgctctg     300
ctaatcctgt taccagtggc tgctgccagt ggcgataagt cgtgtcttac cgggttggac     360
tcaagacgat agttaccgga taaggcgcag cggtcgggct gaacggggggg ttcgtgcaca     420
cagcccagct tggagcgaac gacctacacc gaactgagat acctacagcg tgagctatga     480
gaaagcgcca cgcttcccga agggagaaag gcggacaggt atccggtaag cggcagggtc     540
ggaacaggag agcgcacgag ggagcttcca gggggaaacg cctggtatct ttatagtcct     600
gtcgggtttc gccacctctg acttgagcgt cgatttttgt gatgctcgtc agggggggcgg     660
agcctatgga aaaacgccag caacgcggcc ttttacggt tcctggcctt ttgctggcct      720
tttgctcaca tgtgtgctgg gccccaatgc cttctccaag ggcggcattc ccctgactgt     780
tgaaggcgtt gccaatatca agattgctgg ggaagaaccg accatccaca acgcgatcga     840
gcggctgctt ggcaaaaacc gtaaggaaat cgagcaaatt gccaaggaga ccctcgaagg     900
caacttgcgt ggtgttttag ccagcctcac gccggagcag atcaacgagg acaaaattgc     960
ctttgccaaa agtctgctgg aagaggcgga ggatgacctt gagcagctgg gtcaagtcct    1020
cgatacgctg caagtccaga acatttccga tgaggtcggt tatctctcgg ctagtggacg    1080
caagcagcgg gctgatctgc agcgagatgc ccgaattgct gaagccgatg cccaggctgc    1140
ctctgcgatc caaacggccg aaaatgacaa gatcacggcc ctgcgtcgga tcgatcgcga    1200
tgtagcgatc gcccaagccg aggccgagcg ccggattcag gatgcgttga cgcggcgcga    1260
agcggtggtg gccgaagctg aagcggacat tgctaccgaa gtcgctcgta gccaagcaga    1320
actccctgtg cagcaggagc ggatcaaaca ggtgcagcag caacttcaag ccgatgtgat    1380
cgccccagct gaggcagctt gtaaacgggc gatcgcggaa gcgcgggggg ccgccgcccg    1440
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
```

```
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga agcggtgatc    1920
gccgaagtat cgactcaact atcagaggta gttggcgtca tcgagcgcca tctcgaaccg    1980
acgttgctgg ccgtacattt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aacctttcgc ggtatggcat    2760
gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca atcgcgctgt tagcgggcc    3360 cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag ggcaatcagc tgttgcccgt ctcactggtg aaaagaaaaa    3780
ccaccctggc gcccaatacg caaaccgcct ctccccgcgc gttggccgat tcattaatgc    3840
agctggcacg acaggtttcc cgactggaaa gcggcagtga gcgcaacgc aattaatgta    3900 agttagcgcg aattgatctg gtttgacagc ttatcatcga ctgcacggtg caccaatgct    3960
tctggcgtca ggcagccatc ggaagctgtg gtatggctgt gcaggtcgta aatcactgca    4020
taattcgtgt cgctcaaggc gcactcccgt tctggataat gttttttgcg ccgacatcat    4080
```

```
aacggttctg gcaaatattc tgaaatgagc tgttgacaat taatcatccg gctcgtataa    4140
tgtgtggaat tgtgagcgga taacaatttc agaattcaaa agatctaaag aggagaaata    4200
ctagatgagc tttgatatcg ccaaatacccc caccctggcc ctggtggata gcacccagga   4260
actgcgcctg ctgcccaaag aaagcctgcc caaactgtgc gatgaactgc gccgctacct    4320
gctggatagc gtgagccgca gcagcggcca cttttgccagc ggcctgggca ccgtggaact   4380
gaccgtggcc ctgcactacg tgtacaacac cccctttgat cagctgatct gggatgtggg    4440
ccaccaggcc taccccccaca aaatcctgac cggccgccgc gataaaatcg gcaccatccg    4500
ccagaaaggc ggcctgcacc cctttccctg gcgcggcgaa agcgaatacg atgtgctgag    4560
cgtgggccac agcagcacca gcatcagcgc cggcatcggc atcgccgtgg ccgccgaaaa    4620
agaaggcaaa aaccgccgca ccgtgtgcgt gatcggcgat ggcgccatca ccgccggcat    4680
ggcctttgaa gccatgaacc acgccggcga tatccgcccc gatatgctgg tgatcctgaa    4740
cgataacgaa atgagcatca gcgaaaacgt gggcgcccctg aacaaccacc tggcccagct    4800
gctgagcggc aaactgtaca gcagcctgcg cgaaggcggc aaaaaagtgt ttagcggcgt    4860
gccccccatc aaagaactgc tgaaacgcac cgaagaacac atcaaaggca tggtggtgcc    4920 cggcacccctg tttgaagaac tgggcttttaa ctacatcggc cccgtggatg ccacgatgt    4980 gctgggcctg atcaccaccc tgaaaaacat gcgcgatctg aaaggccccc agttcctgca    5040
tatcatgacc aaaaaaggcc gcggctacga acccgccgaa aaagatccca tcaccttttca    5100 cgccgtgccc aaatttgatc cagcagcgg ctgcctgccc aaaagcagcg gcggcctgcc    5160
cagctacagc aaaatctttg gcgattggct gtgcgaaacc gccgccaaag ataacaaact   5220
gatggccatc accccccgcca tgcgcgaagg cagcggcatg gtggaatta gccgcaaatt    5280 tcccgatcgc tactttgatg tggccatcgc cgaacagcac gccgtgacct ttgccgccgg    5340
cctggccatc ggcggctaca aacccatcgt ggccatctac agcacctttc tgcagcgcgc    5400
ctacgatcag gtgctgcacg atgtggccat ccagaaactg cccgtgctgt ttgccatcga    5460
tcgcgccggc atcgtgggcg ccgatggcca gacccaccag ggcgcctttg atctgagcta    5520
cctgcgctac atccccgaaa tggtgatcat gaccccccagc gatgaaaacg aatgccgcca    5580
gatgctgtac accggctacc actacaacga tggccccagc gccgtgcgct accccccgcgg    5640 caacgccgtg ggcgtggaac tgacccccct ggaaaaactg cccatcggca aaggcatcgt    5700
gaaacgccgc ggcgaaaaac tggccatcct gaactttggc accctgatgc ccgaagccgc    5760
caaagtggcc gaaagcctga cgccaccct ggtggatatg cgctttgtga acccctggga    5820
tgaagccctg atcctggaaa tggccgccag ccacgaagcc ctggtgaccg tggaagaaaa    5880
cgccatcatg ggcggcgccg gcagcggcgt gaacgaagtg ctgatggccc accgcaaacc    5940 cgtgccgtg ctgaacatcg gcctgcccga ttttttttatc ccccagggca cccaggaaga   6000
aatgcgcgcc gaactgggcc tggatgccgc cggcatggaa gccaaaatca agcctggct    6060 ggcctaggga tctattaaag aggagaatac tagatgaaac agctgaccat cctgggcagc    6120
accggcagca tcggcgtgcag caccctggat gtggtgcgcc acaacccccga cacttccgc    6180 gtggtggccc tggtggccgg caaaaacgtg accgcatgg tgaacagtg cctggaattt    6240 agcccccgct acgccgtgat ggatgatgaa gccagcgcca aactgctgaa aaccatgctg    6300
cagcagcagg gcagccgcac cgaagtgctg agcggccagc aggccgcctg cgatatggcc    6360
gccctggaag atgtggatca ggtgatggcc gccatcgtgg gcgccgccgg cctgctgccc    6420
accctggccg ccatccgcgc cggcaaaacc atcctgctgg ccaacaaaga aagcctggtg    6480
```

```
acctgcggcc gcctgtttat ggatgccgtg aaacagagca aagcccagct gctgcccgtg    6540
gatagcgaac acaacgccat ctttcagagc ctgccccagc ccatccagca caacctgggc    6600
tacgccgatc tggaacagaa cggcgtggtg agcatcctgc tgaccggcag cggcggcccc    6660
tttcgcgaaa ccccctgcg cgatctggcc accatgaccc ccgatcaggc ctgccgccac    6720
cccaactgga gcatgggccg caaaatcagc gtggatagcg ccaccatgat gaacaaaggc    6780
ctggaataca tcgaagcccg ctggctgttt aacgccagcg ccagccagat ggaagtgctg    6840
atccaccccc agagcgtgat ccacagcatg gtgcgctacc aggatggcag cgtgctggcc    6900
cagctgggcg aacccgatat cgcaccccc atcgcccaca ccatggcctg cccaaccgc    6960
gtgaacagcg gcgtgaaacc cctggatttt tgcaaactga gcgccctgac ctttgccgcc    7020
cccgattacg atcgctaccc ctgcctgaaa ctggccatgg aagcctttga cagggccag    7080
gccgccacca ccgccctgaa cgccgccaac gaaatcaccg tggccgcctt tctggcccag    7140
cagatccgct ttaccgatat cgccgccctg aacctgagcg tgctggaaaa aatggatatg    7200
cgcgaacccc agtgcgtgga tgatgtgctg agcgtggatg ccaacgcccg cgaagtggcc    7260
cgcaaagaag tgatgcgcct ggccagctag ggatctaaag aggagaaata ctagatgcag    7320
accgaacacg tgatcctgct gaacgcccag ggcgtgccca ccggcaccct ggaaaaatac    7380
gccgcccaca ccgccgatac ccgcctgcac ctggccttta gcagctggct gtttaacgcc    7440
aaaggccagc tgctggtgac ccgccgcgcc ctgagcaaaa agcctggcc cggcgtgtgg    7500
accaacagcg tgtgcggcca ccccagctg ggcgaaagca cgaagatgc cgtgatccgc    7560
cgctgccgct acgaactggg cgtggaaatc accccccccg aaagcatcta ccccgatttt    7620
cgctaccgcg ccaccgatcc cagcggcatc gtggaaaacg aagtgtgccc cgtgtttgcc    7680
gcccgcacca ccagcgccct gcagatcaac gatgatgaag tgatggatta ccagtggtgc    7740
gatctggccg atgtgctgca cggcatcgat gccacccct gggcctttag cccctggatg    7800
gtgatgcagg ccaccaaccg cgaagcccgc aaacgcctga cgccttta ccagctgaaa    7860
tagggatcta ttaaagagga gaatactaga tggattttcc ccagcagctg gaagcctgcg    7920
tgaaacaggc caaccaggcc ctgagccgct ttatcgcccc cctgcccttt cagaacaccc    7980
ccgtggtgga aaccatgcag tacgcgcccc tgctgggcgg caaacgcctg cgccccttc    8040
tggtgtacgc caccggccac atgtttggcg tgagcaccaa caccctggat gccccgccg    8100
ccgccgtgga atgcatccac gcctacagcc tgatccacga tgatctgccc gccatggatg    8160
atgatgatct cgccgcggc ctgcccacct gccacgtgaa atttggcgaa gccaacgcca    8220
tcctggccgg cgatgccctg cagaccctgg cctttagcat cctgagcgat gccgatatgc    8280
ccgaagtgag cgatcgcgat cgcatcagca tgatcagcga actggccagc ccagcggca    8340
tcgccggcat gtgcggcggc caggccctgg atctggatgc cgaaggcaaa cacgtgcccc    8400
tggatgccct ggaacgcatc caccgccaca aaaccggcgc cctgatccgc gccgccgtgc    8460
gcctgggcgc cctgagcgcc ggcgataaag ccgccgcgc cctgccgtg ctggataaat    8520
acgccgaaag catcggcctg gcctttcagg tgcaggatga tatcctggat gtggtgggcg    8580
ataccgccac cctgggcaaa cgccagggcg ccgatcagca gctgggcaaa agcacctacc    8640
ccgccctgct gggcctggaa caggcccgca aaaagcccg cgatctgatc gatgatgccc    8700
gccagagcct gaaacagctg gccgaacaga gcctggatac cagcgccctg aagcccctgg    8760
ccgattacat catccagcgc aacaaatagg gatccaaact cgagtaagga tctccaggca    8820
```

| | |
|---|---|
| tcaaataaaa cgaaaggctc agtcgaaaga ctgggccttt cgttttatct gttgtttgtc | 8880 |
| ggtgaacgct ctctactaga gtcacactgg ctcaccttcg ggtgggcctt tctgcgttta | 8940 |
| tacctagggc gttcggctgc ggcgagcggt atcagctcac tcaaaggcgg taatacgtcc | 9000 |
| ctgctcgtca cgctttcagg caccgtgcca gatatcgacg tggagtcgat cactgtgatt | 9060 |
| ggcgaagggg aaggcagcgc tacccaaatc gctagcttgc tggagaagct gaaacaaacc | 9120 |
| acgggcattg atctggcgaa atccctaccg ggtcaatccg actcgcccgc tgcgaagtcc | 9180 |
| taagagatag cgatgtgacc gcgatcgctt gtcaagaatc ccagtgatcc cgaaccatag | 9240 |
| gaaggcaagc tcaatgcttg cctcgtcttg aggactatct agatgtctgt ggaacgcaca | 9300 |
| tttattgcca tcaagcccga tggcgttcag cggggtttgg tcggtacgat catcggccgc | 9360 |
| tttgagcaaa aaggcttcaa actggtgggc ctaaagcagc tgaagcccag tcgcgagctg | 9420 |
| gccgaacagc actatgctgt ccaccgcgag cgccccttct tcaatggcct cgtcgagttc | 9480 |
| atcacctctg ggccgatcgt ggcgatcgtc ttggaaggcg aaggcgttgt ggcggctgct | 9540 |
| cgcaagttga tcggcgctac caatccgctg acggcagaac cgggcaccat ccgtggtgat | 9600 |
| tttggtgtca atattggccg caacatcatc catggctcgg atgcaatcga aacagcacaa | 9660 |
| caggaaattg ctctctggtt tagcccagca gagctaagtg attggacccc cacgattcaa | 9720 |
| ccctggctgt acgaataagg tctgcattcc ttcagagaga cattgccatg ccg | 9773 |

<210> SEQ ID NO 9
<211> LENGTH: 7472
<212> TYPE: DNA
<213> ORGANISM: Artificial Sequence
<220> FEATURE:
<223> OTHER INFORMATION: pSe2Bb1k-sqs vector(sqs gene is drirved from Saccharomyces cerevisiae)

<400> SEQUENCE: 9

| | |
|---|---|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| cttttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |
| tcaagacgat agttaccgga taaggcgcag cggtcgggct gaacggggggg ttcgtgcaca | 420 |
| cagcccagct tggagcgaac gacctacacc gaactgagat acctacagcg tgagctatga | 480 |
| gaaagcgcca cgcttcccga agggagaaag gcggacaggt atccggtaag cggcagggtc | 540 |
| ggaacaggag agcgcacgag ggagcttcca gggggaaacg cctggtatct ttatagtcct | 600 |
| gtcgggtttc gccacctctg acttgagcgt cgatttttgt gatgctcgtc aggggggcgg | 660 |
| agcctatgga aaaacgccag caacgcggcc ttttttacggt tcctggcctt ttgctggcct | 720 |
| tttgctcaca tgtgtgctgg ccccccatca attcatcagc caaatgcccg atggctatga | 780 |
| cacatgggtg ggagagcgcg gcgtcaacct ctccggcggt cagcggcagc ggctggcgat | 840 |
| cgcccgcgcg gtcttgctgg atccacgcat tttaattctg gatgaggcga cttcggcgct | 900 |
| tgattccgag tccgaaacct tggtgcaaga ggccctagaa cgggtgatgc agggacggac | 960 |
| ggtcttatc attgctcacc gtctggctac ggttcgtaat gccagccgca tcttggtgat | 1020 |
| ggagcgcggc cagattgttg aggcaggcaa tcacgatgcg ctgttggcag aggctggccg | 1080 |

```
ctatgcgcga tactacgcac agcaatttcg tgcctgatca ggattaatga aacggacgcc    1140
ccagactgaa ttgccggact gggaagcgat cgcggatttg gatgcgatcg tggtcgataa    1200
acgagctcgt aagcgggcca cggcagcgaa agggcgacgg cgcgatcgcc ggtatggaaa    1260
acgcttgctg cagcatcaga tcgatgcgat cgccgaagac tgtgacctag atgaggaagc    1320
atgagcgaac tgggcttgag tctgacggcg atcgcgattt ttaccacgac ggcattagct    1380
ttggtgggac caatgctggg tagttctccg ctgctaccgg cgggattggg ttttagcctc    1440
ttggtgctgt tcagtctgga tgcggtgact tggcaggggc ggggtgccac gttactgctc    1500
gatggcattc agcagcgatc gcccgaatat cgtcagcgga ttttgcatca cgaagcgggt    1560
cactacttgg tagcaaccgc gctggggtta cccgtgacgg gctacaccct ctcagcgtgg    1620
gaagcgctgc gccaaggaca acctggtcgc ggggtgtgc agttccaagc agctgcgcta    1680
gaagccgaag ccgcacaggg gcaactcagt cagcgatcgc tggaacagtg gtgtcaggtg    1740
ttgatggccg gtgcagcggc agagcaactg gtctacggca acgtggaagg gggagctgac    1800
gatcgcgccc agtggaaaca actgtggcgg caactcgatc gcaatcctgc cgaagcggat    1860
ttacgcagtc gctggggatt gttacgggcg aagactttac tggagcaaca acgtcccgcc    1920
tacgatgctt tggtggcggc gatggctgca gaggccagca ttgaagactg caatcaagcg    1980
atcgccactg cttgggtaga agaacctgcg atcgccgctt agtgaagagt ccagaagatt    2040
cccctcccct ctcgcccaat ggacaaggga aatgtgattc agcatgagtc aagtccccag    2100
tgcatggatg ggtgtgcaat gagagctctc gaaccccaga gtcccgctca agaactcg    2160 tcaagaaggc gatagaaggc gatgcgctgc gaatcgggag cggcgatacc gtaaagcacg    2220
aggaagcggt cagcccattc gccgccaagc tcttcagcaa tatcacgggt agccaacgct    2280
atgtcctgat agcggtccgc cacacccagc cggccacagt cgatgaatcc agaaaagcgg    2340
ccattttcca ccatgatatt cggcaagcag gcatcgccat gggtcacgac gagatcctcg    2400
ccgtcgggca tgcgcgcctt gagcctggcg aacagttcgg ctggcgcgag ccctgatgc    2460 tcttcgtcca gatcatcctg atcgacaaga ccggcttcca tccgagtacg tgctcgctcg    2520
atgcgatgtt tcgcttggtg gtcgaatggg caggtagccg gatcaagcgt atgcagccgc    2580
cgcattgcat cagccatgat ggatactttc tcggcaggag caaggtgaga tgacaggaga    2640
tcctgccccg gcacttcgcc caatagcagc cagtcccttc ccgcttcagt gacaacgtcg    2700
agcacagctg cgcaaggaac gcccgtcgtg gccagccacg atagccgcgc tgcctcgtcc    2760
tgcagttcat tcagggcacc ggacaggtcg gtcttgacaa aaagaaccgg gcgccctgc    2820 gctgacagcc ggaacacggc ggcatcagag cagccgattg tctgttgtgc ccagtcatag    2880
ccgaatagcc tctccaccca gcggccgga gaacctgcgt gcaatccatc ttgttcaatc    2940
atgcgaaacg atcctcatcc tgtctcttga tcagatcatg atccctgcg ccatcagatc    3000 cttggcggca agaaagccat ccagtttact ttgcagggct tcccaacctt accagagggc    3060
gccccagctg gcaattccga cgtcgacacc atcgaatggt gcaaaacctt tcgcggtatg    3120
gcatgatagc gcccggaaga gagtcaattc agggtggtga atgtgaaacc agtaacgtta    3180
tacgatgtcg cagagtatgc cggtgtctct tatcagaccg tttcccgcgt ggtgaaccag    3240
gccagccacg tttctgcgaa aacgcgggaa aaagtggaag cggcgatggc ggagctgaat    3300
tacattccca accgcgtggc acaacaactg gcggcaaac agtcgttgct gattggcgtt    3360
gccacctcca gtctggccct gcacgcgccg tcgcaaattg tcgcggcgat taaatctcgc    3420
gccgatcaac tgggtgccag cgtggtggtg tcgatggtag aacgaagcgg cgtcgaagcc    3480
```

```
tgtaaagcgg cggtgcacaa tcttctcgcg caacgcgtca gtgggctgat cattaactat    3540
ccgctggatg accaggatgc cattgctgtg gaagctgcct gcactaatgt tccggcgtta    3600
tttcttgatg tctctgacca gacacccatc aacagtatta ttttctccca tgaagacggt    3660
acgcgactgg gcgtggagca tctggtcgca ttgggtcacc agcaaatcgc gctgttagcg    3720
ggcccattaa gttctgtctc ggcgcgtctg cgtctggctg gctggcataa atatctcact    3780
cgcaatcaaa ttcagccgat agcggaacgg gaaggcgact ggagtgccat gtccggtttt    3840
caacaaacca tgcaaatgct gaatgagggc atcgttccca ctgcgatgct ggttgccaac    3900
gatcagatgg cgctgggcgc aatgcgcgcc attaccgagt ccgggctgcg cgttggtgcg    3960
gatatctcgg tagtgggata cgacgatacc gaagacagct catgttatat cccgccgtta    4020
accaccatca acaggatttt cgcctgctg gggcaaacca gcgtggaccg cttgctgcaa    4080
ctctctcagg gccaggcggt gaagggcaat cagctgttgc ccgtctcact ggtgaaaaga    4140
aaaaccaccc tggcgcccaa tacgcaaacc gcctctcccc gcgcgttggc cgattcatta    4200
atgcagctgg cacgacaggt ttcccgactg gaaagcgggc agtgagcgca acgcaattaa    4260
tgtaagttag cgcgaattga tctggtttga cagcttatca tcgactgcac ggtgcaccaa    4320
tgcttctggc gtcaggcagc catcggaagc tgtggtatgg ctgtgcaggt cgtaaatcac    4380
tgcataattc gtgtcgctca aggcgcactc ccgttctgga taatgttttt tgcgccgaca    4440
tcataacggt tctggcaaat attctgaaat gagctgttga caattaatca tccggctcgt    4500
ataatgtgtg gaattgtgag cggataacaa tttcagggga attcaaaaga tctataaaag    4560
taaagaagga gaccataaat gggcaaactg ctgcagctgg ccctgcaccc cgtggaaatg    4620
aaagccgccc tgaaactgaa attttgccgc accccctgt ttagcatcta cgatcagagc    4680
accagcccct acctgctgca ctgctttgaa ctgctgaacc tgaccagccg cagctttgcc    4740
gccgtgatcc gcgaactgca ccccgaactg cgcaactgcg tgaccctgtt ttacctgatc    4800
ctgcgcgccc tggataccat cgaagatgat atgagcatcg aacacgatct gaaaatcgat    4860
ctgctgcgcc actttcacga aaaactgctg ctgaccaaat ggagctttga tggcaacgcc    4920
cccgatgtga aagatcgcgc cgtgctgacc gattttgaaa gcatcctgat cgaatttcac    4980
aaactgaaac ccgaatacca ggaagtgatc aaagaaatca ccgaaaaaat gggcaacggc    5040
atggccgatt acatcctgga tgaaaactac aacctgaacg gcctgcagac cgtgcacgat    5100
tacgatgtgt actgccacta cgtggccggc ctggtgggcg atggcctgac ccgcctgatc    5160
gtgatcgcca aatttgccaa cgaaagcctg tacagcaacg aacagctgta cgaaagcatg    5220
ggcctgtttc tgcagaaaac caacatcatc cgcgattaca acgaggatct ggtggatggc    5280
cgcagctttt ggcccaaaga aatctggagc cagtacgccc ccagctgaa agattttatg    5340 aaacccgaaa acgaacagct gggcctggat tgcatcaacc acctggtgct gaacgccctg    5400
agccacgtga tcgatgtgct gacctacctg gccggcatcc acgaacagag cacctttcag    5460
ttttgcgcca tcccccaggt gatggccatc gccaccctgg ccctggtgtt taacaaccgc    5520
gaagtgctgc acggcaacgt gaaaatccgc aaaggcacca cctgctacct gatcctgaaa    5580
agccgcaccc tgcgcggctg cgtggaaatc tttgattact acctgcgcga tatcaaaagc    5640
aaactggccg tgcaagatcc caactttctg aaactgaaca tccagatcag caaaatcgaa    5700
cagtttatgg aagaaatgta ccaggataaa ctgccccca acgtgaaacc caacgaaacc    5760
cccatctttc tgaaagtgaa agaacgcagc cgctacgatg atgaactggt gcccacccag    5820
```

| | |
|---|---:|
| caggaagaag aatacaaata gggatccaaa ctcgagtaag gatctccagg catcaaataa | 5880 |
| aacgaaaggc tcagtcgaaa gactgggcct ttcgttttat ctgttgtttg tcggtgaacg | 5940 |
| ctctctacta gagtcacact ggctcacctt cgggtgggcc tttctgcgtt tatacctagg | 6000 |
| gcgttcggct gcggcgagcg gtatcagctc actcaaaggc ggtaatacgg gcaattcaag | 6060 |
| agcatccaaa gcctcttcaa ccccaggaac ggcttgtaga tgcgtttcta acgcgatacg | 6120 |
| ggtacggcgt tgatagtgct gaacaaagtc aggggggtgga ggattgccta accgtcgctc | 6180 |
| aattagtttg agacagtcag ccatggaatg acccacaaac tgctcaaaca tgtcatccaa | 6240 |
| agtcaccaac agaccccagtt cattgagcat gtctgcaaag acgcgattag tgatgcgttc | 6300 |
| gctatcaaca agcacaccat cacagtcgaa aatcaccagc tgaaacggtg aagtttgcat | 6360 |
| tgttttttaag cacgagccat caacagtaag agcgatcgcg ctgggacgat gtaatcgcgc | 6420 |
| cgtaggcagg gttttgcctc atccggcaga tgacaagctt caagattcgg cagtgaagta | 6480 |
| tcgagcaagc gataccaaac gcggccgcga ggaggcctcg gcaactggaa gcgcaggtct | 6540 |
| tcccagtaag cattaaaggc taggtaaagc cattcctgct ggcgaggatg gcagagactg | 6600 |
| acggccagac tgtgggacca cagcgcccaa tcgggttgtt tgagtttgac gccatgccag | 6660 |
| atggcatagg gacgacgcgg atggggttcg ttctgcagca gttcgttctg ttggaacatc | 6720 |
| accagcgact gggaaagttc aatcaggcgg cgactgaaca ccaagaaatc ggcatggcga | 6780 |
| tcgcacagcg accaatcaaa ccagctgatc tcattgtctt ggcagtaggc gttattgtta | 6840 |
| ccctgctgac tgcgtttgac ctcatcgccc atcgtcagca tcggtgtgcc ctgggcgagg | 6900 |
| aataacgtgg cgagcaaatt gcgctgctgc cgttcccgta agctcagaat cgtgggtca | 6960 |
| tcggtctcgc cttcaatgcc gtagttccag ctgtagttgt cattggtccc gtcccgattg | 7020 |
| ttctctccat tggcaaagtt gtgcttctgg ctatagctga ctagatctcg cagcgtaaag | 7080 |
| ccgtcatggc aggtgatgaa gttaatggtg cgtccggcat accattggtc tgtgctgtag | 7140 |
| acatcggggc tacccagcag gcgttgactg agggcgtaag tacagccctg atctccacgc | 7200 |
| caaaaacgcc gaatatcgtc ccggaaggga ccgttccaag tcccaaagcg atcgccaata | 7260 |
| aaggtaccaa cctgatataa gccggctgcg tcccaagctt cagcaatgag cttcgtaccg | 7320 |
| gccaaaaccg gatcggaatc aatcgcccaa agcaagggcg gatccgatag ggggttgcca | 7380 |
| ttggcatcac gactcagcac cgacgcaagg tcaaagcgga agccatcgac gtgcatttcc | 7440 |
| gagacccaat aacgcaggca atcgagaatc ag | 7472 |

<210> SEQ ID NO 10
<211> LENGTH: 7298
<212> TYPE: DNA
<213> ORGANISM: Artificial Sequence
<220> FEATURE:
<223> OTHER INFORMATION: pSe2Bb1k-sqs vector(sqs gene is drirved from Methylococcus capsulatus)

<400> SEQUENCE: 10

| | |
|---|---:|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| cttttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |

-continued

```
tcaagacgat agttaccgga taaggcgcag cggtcgggct gaacgggggg ttcgtgcaca      420
cagcccagct tggagcgaac gacctacacc gaactgagat acctacagcg tgagctatga      480
gaaagcgcca cgcttcccga agggagaaag gcggacaggt atccggtaag cggcagggtc      540
ggaacaggag agcgcacgag ggagcttcca gggggaaacg cctggtatct ttatagtcct      600
gtcgggtttc gccacctctg acttgagcgt cgattttgt gatgctcgtc agggggcgg        660 agcctatgga aaaacgccag caacgcggcc tttttacggt tcctggcctt ttgctggcct      720
tttgctcaca tgtgtgctgg ccccccatca attcatcagc caaatgcccg atggctatga      780
cacatgggtg ggagagcgcg cgtcaacct ctccggcggt cagcggcagc ggctggcgat       840
cgcccgcgcg gtcttgctgg atccacgcat tttaattctg gatgaggcga cttcggcgct      900
tgattccgag tccgaaacct tggtgcaaga ggccctagaa cgggtgatgc agggacggac      960
ggtctttatc attgctcacc gtctggctac ggttcgtaat gccagccgca tcttggtgat     1020
ggagcgcggc cagattgttg aggcaggcaa tcacgatgcg ctgttggcag aggctggccg     1080
ctatgcgcga tactacgcac agcaatttcg tgcctgatca ggattaatga aacggacgcc     1140
ccagactgaa ttgccggact gggaagcgat cgcggatttg gatgcgatcg tggtcgataa     1200
acgagctcgt aagcgggcca cggcagcgaa agggcgacgg cgcgatcgcc ggtatggaaa     1260
acgcttgctg cagcatcaga tcgatgcgat cgccgaagac tgtgacctag atgaggaagc     1320
atgagcgaac tgggcttgag tctgacgcg atcgcgattt ttaccacgac ggcattagct      1380
ttggtgggac caatgctggg tagttctccg ctgctaccgg cgggattggg ttttagcctc     1440
ttggtgctgt tcagtctgga tgcggtgact tggcaggggc ggggtgccac gttactgctc     1500
gatggcattc agcagcgatc gcccgaatat cgtcagcgga ttttgcatca cgaagcgggt     1560
cactacttgg tagcaaccgc gctggggtta cccgtgacgg gctacaccct ctcagcgtgg     1620
gaagcgctgc gccaaggaca acctggtcgc ggggtgtgc agttccaagc agctgcgcta     1680
gaagccgaag ccgcacaggg gcaactcagt cagcgatcgc tggaacagtg gtgtcaggtg     1740
ttgatggccg gtgcagcggc agagcaactg gtctacggca acgtggaagg gggagctgac     1800
gatcgcgccc agtggaaaca actgtggcgg caactcgatc gcaatcctgc cgaagcggat     1860
ttacgcagtc gctggggatt gttacgggcg aagactttac tggagcaaca acgtcccgcc     1920
tacgatgctt tggtggcggc gatggctgca gaggccagca ttgaagactg caatcaagcg     1980
atcgccactg cttgggtaga agaacctgcg atcgccgctt agtgaagagt ccagaagatt     2040
cccctcccct ctcgcccaat ggacaaggga aatgtgattc agcatgagtc aagtccccag     2100
tgcatggatg ggtgtgcaat gagagctctc gaaccccaga gtcccgctca gaagaactcg     2160
tcaagaaggc gatagaaggc gatgcgctgc gaatcgggag cggcgatacc gtaaagcacg     2220
aggaagcggt cagcccattc gccgccaagc tcttcagcaa tatcacgggt agccaacgct     2280
atgtcctgat agcggtccgc cacacccagc cggccacagt cgatgaatcc agaaaagcgg     2340
ccattttcca ccatgatatt cggcaagcag gcatcgccat gggtcacgac gagatcctcg     2400
ccgtcgggca tgcgcgcctt gagcctggcg aacagttcgg ctggcgcgag cccctgatgc     2460
tcttcgtcca gatcatcctg atcgacaaga ccggcttcca tccgagtacg tgctcgctcg     2520
atgcgatgtt tcgcttggtg gtcgaatggg caggtagccg gatcaagcgt atgcagccgc     2580
cgcattgcat cagccatgat ggatactttc tcggcaggag caaggtgaga tgacaggaga     2640
tcctgccccg gcacttcgcc caatagcagc cagtcccttc ccgcttcagt gacaacgtcg     2700
agcacagctg cgcaaggaac gcccgtcgtg gccagccacg atagccgcgc tgcctcgtcc     2760
```

```
tgcagttcat tcagggcacc ggacaggtcg gtcttgacaa aaagaaccgg gcgcccctgc    2820
gctgacagcc ggaacacggc ggcatcagag cagccgattg tctgttgtgc ccagtcatag    2880
ccgaatagcc tctccaccca agcggccgga gaacctgcgt gcaatccatc ttgttcaatc    2940
atgcgaaacg atcctcatcc tgtctcttga tcagatcatg atccctgcg ccatcagatc     3000 cttggcggca agaaagccat ccagtttact ttgcagggct tcccaacctt accagagggc    3060
gccccagctg gcaattccga cgtcgacacc atcgaatggt gcaaaacctt tcgcggtatg    3120
gcatgatagc gcccggaaga gagtcaattc agggtggtga atgtgaaacc agtaacgtta    3180
tacgatgtcg cagagtatgc cggtgtctct tatcagaccg tttccgcgt ggtgaaccag     3240 gccagccacg tttctgcgaa aacgcgggaa aaagtggaag cggcgatggc ggagctgaat    3300
tacattccca accgcgtggc acaacaactg gcgggcaaac agtcgttgct gattggcgtt    3360
gccacctcca gtctggccct gcacgcgccg tcgcaaattg tcgcggcgat taaatctcgc    3420
gccgatcaac tgggtgccag cgtggtggtg tcgatggtag aacgaagcgg cgtcgaagcc    3480
tgtaaagcgg cggtgcacaa tcttctcgcg caacgcgtca gtgggctgat cattaactat    3540
ccgctggatg accaggatgc cattgctgtg gaagctgcct gcactaatgt tccggcgtta    3600
tttcttgatg tctctgacca gacacccatc aacagtatta ttttctccca tgaagacggt    3660
acgcgactgg gcgtggagca tctggtcgca ttgggtcacc agcaaatcgc gctgttagcg    3720
ggcccattaa gttctgtctc ggcgcgtctg cgtctggctg gctggcataa atatctcact    3780
cgcaatcaaa ttcagccgat agcggaacgg gaaggcgact ggagtgccat gtccggtttt    3840
caacaaacca tgcaaatgct gaatgagggc atcgttccca ctgcgatgct ggttgccaac    3900
gatcagatgg cgctgggcgc aatgcgcgcc attaccgagt ccgggctgcg cgttggtgcg    3960
gatatctcgg tagtgggata cgacgatacc gaagacagct catgttatat cccgccgtta    4020
accaccatca acaggatttt cgcctgctg gggcaaacca gcgtggaccg cttgctgcaa     4080
ctctctcagg gccaggcggt gaagggcaat cagctgttgc ccgtctcact ggtgaaaaga    4140
aaaaccaccc tggcgcccaa tacgcaaacc gcctctcccc gcgcgttggc cgattcatta    4200
atgcagctgg cacgacaggt ttcccgactg gaaagcgggc agtgagcgca acgcaattaa    4260
tgtaagttag cgcgaattga tctggtttga cagcttatca tcgactgcac ggtgcaccaa    4320
tgcttctggc gtcaggcagc catcggaagc tgtggtatgg ctgtgcaggt cgtaaatcac    4380
tgcataattc gtgtcgctca aggcgcactc ccgttctgga taatgttttt tgcgccgaca    4440
tcataacggt tctggcaaat attctgaaat gagctgttga caattaatca tccggctcgt    4500
ataatgtgtg gaattgtgag cggataacaa tttcaggaat tcaaaagatc taagattacg    4560
taacgaagga gagaaaccat gagcggcacc ccccccagcc agcccgcccg ccacgaacac    4620
ctgagcgatg atgaatttca ggcccacttt ctggatggcg tgagccgcac ctttgccctg    4680
accatccccc gcctgcccga aggcctgccc cgccccgtga gcaacggcta cctgctgtgc    4740
cgcatcgtgg ataccatcga agatgaagtg gccctgacca gcacccagaa acgccgctac    4800
tgcgaacact ttgcccgcgt ggtggccggc accgcccccg ccgcccccct ggccgatgaa    4860
ctgtttcccc tgctgagcga tcagaccctg gccgccgaac gcgaactgat cgccgccatc    4920
ccccgcgtga tcagcatcac ccacggcttt gccgccccc agcaggaagc cctggccgaa     4980
tgcgtggcca ccatgagccg cggcatggcc gaatttcagg ataaggatct gcgccacggc    5040
ctggaggatc tgcgccagat gggcgattac tgctactacg tggccggcgt ggtgggcgaa    5100
```

```
atgctgaccc gcctgttttg ccactacagc cccgaaatcg ccgcccaccg cagccgcctg    5160
atggaactgg cctgcccctt tggccagggc ctgcagatga ccaacatcct gaaggatctg    5220
tgggatgatc acgcccgcgg cgtgtgctgg ctgccccagg aagtgtttac cgaatgcggc    5280
tttagcctga ccgaactgcg ccccaccac gccaacccg attttgtgcg cggctttgaa      5340
cgcctgatcg gcgtggccca cgcccacctg cgcaacgccc tggaatacac cctgctgatc    5400
ccccgccacg aaaccggcat ccgcgaattt tgcctgtggg ccctgggcat ggccgtgctg    5460
accctgcgca aaatccaccg ccaccctac tttagcgata cgcccaggt gaaaatcacc     5520 cgccaggccg tgaaagccac catcgtgacc agccgcctga cccgcggcag cgataccctg   5580
ctgaaagcca ccttcgcct ggccggcctg ggcctgcccg ccgccgtgcc cgccgccgtg    5640
ctgcagcccc gccccatcga tatctaggga tccaaactcg agtaaggatc tccaggcatc    5700
aaataaaacg aaaggctcag tcgaaagact gggcctttcg ttttatctgt tgtttgtcgg    5760
tgaacgctct ctactagagt cacactggct caccttcggg tgggcctttc tgcgtttata    5820
cctagggcgt tcggctgcgg cgagcggtat cagctcactc aaaggcggta atacgggcaa    5880
ttcaagagca tccaaagcct cttcaacccc aggaacggct tgtagatgcg tttctaacgc    5940
gatacgggta cggcgttgat agtgctgaac aaagtcaggg ggtggaggat tgcctaaccg    6000
tcgctcaatt agtttgagac agtcagccat ggaatgaccc acaaactgct caaacatgtc    6060
atccaaagtc accaacagac ccagttcatt gagcatgtct gcaaagacgc gattagtgat    6120
gcgttcgcta tcaacaagca caccatcaca gtcgaaaatc accagctgaa acggtgaagt    6180
ttgcattgtt tttaagcacg agccatcaac agtaagagcg atcgcgctgg gacgatgtaa    6240
tcgcgccgta ggcagggttt tgcctcatcc ggcagatgac aagcttcaag attcggcagt    6300
gaagtatcga gcaagcgata ccaaacgcgg ccgcgaggag gcctcggcaa ctggaagcgc    6360
aggtcttccc agtaagcatt aaaggctagg taaagccatt cctgctggcg aggatggcag    6420
agactgacgg ccagactgtg ggaccacagc gcccaatcgg gttgtttgag tttgacgcca    6480
tgccagatgg cataggacg acgcggatgg ggttcgttct gcagcagttc gttctgttgg    6540
aacatcacca gcgactggga agttcaatc aggcggcgac tgaacaccaa gaaatcggca    6600
tggcgatcgc acagcgacca atcaaaccag ctgatctcat tgtcttggca gtaggcgtta    6660
ttgttaccct gctgactgcg tttgacctca tcgcccatcg tcagcatcgg tgtgccctgg    6720
gcgaggaata acgtggcgag caaattgcgc tgctgccgtt cccgtaagct cagaatcgtg    6780
gggtcatcgg tctcgccttc aatgccgtag ttccagctgt agttgtcatt ggtcccgtcc    6840
cgattgttct ctccattggc aaagttgtgc ttctggctat agctgactag atctcgcagc    6900
gtaaagccgt catggcaggt gatgaagtta atggtgcgtc cggcatacca ttggtctgtg    6960
ctgtagacat cggggctacc cagcaggcgt tgactgaggg cgtaagtaca gccctgatct    7020
ccacgccaaa aacgccgaat atcgtcccgg aagggaccgt tccaagtccc aaagcgatcg    7080
ccaataaagg taccaacctg atataagccg gctgcgtccc aagcttcagc aatgagcttc    7140
gtaccggcca aaaccggatc ggaatcaatc gcccaaagca agggcggatc cgataggggg    7200
ttgccattgg catcacgact cagcaccgac gcaaggtcaa agcggaagcc atcgacgtgc    7260
atttccgaga cccaataacg caggcaatcg agaatcag                           7298
```

<210> SEQ ID NO 11
<211> LENGTH: 25
<212> TYPE: DNA
<213> ORGANISM: Artificial Sequence -continued

```
<220> FEATURE:
<223> OTHER INFORMATION: Primer(forward)

<400> SEQUENCE: 11
ccagcagcgg ctgcctgccc aaaag                                            25

<210> SEQ ID NO 12
<211> LENGTH: 20
<212> TYPE: DNA
<213> ORGANISM: Artificial Sequence
<220> FEATURE:
<223> OTHER INFORMATION: Primer(reverse)

<400> SEQUENCE: 12
gaaagcgtga cgagcaggga                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer(forward)

<400> SEQUENCE: 13
ggctacggtt cgtaatgcca                                                  20

<210> SEQ ID NO 14
<211> LENGTH: 20
<212> TYPE: DNA
<213> ORGANISM: Artificial Sequence
<220> FEATURE:
<223> OTHER INFORMATION: Primer(reverse)

<400> SEQUENCE: 14
gagatcaggg ctgtacttac                                                  20
```

TRANSFORMED *SYNECHOCOCCUS ELONGATUS* STRAIN HAVING CAPABILITY OF PRODUCING SQUALENE FROM CARBON DIOXIDE AND METHOD FOR PRODUCING SQUALENE USING THE SAME

CROSS-REFERENCE TO RELATED APPLICATION

This application claims priority to Korean Patent Application No. 10-2016-0041774, filed on Apr. 5, 2016, and all the benefits accruing therefrom under 35 U.S.C. § 119, the contents of which in its entirety are herein incorporated by reference.

BACKGROUND

1. Field

The present specification discloses a transformed *Synechococcus elongatus* strain which may mass-produce squalene from carbon dioxide, and a method for producing squalene and a method for removing carbon dioxide, using the same.

DESCRIPTION ABOUT NATIONAL SUPPORT RESEARCH AND DEVELOPMENT

This study is made by the support of KOREA CCS 2020 business of the Korean Ministry of Science, ICT and Future Planning under the supervision of the Korea Institute of Science and Technology, and the subject name thereof is Development of original technology of using recombinant cyanobacteria for continuous direct production of biodiesel (Subject Identification No.: 2015030270).

2. Description of the Related Art

Squalene is a triterpenoid-based unsaturated hydrocarbon in which 30 carbon atoms and 50 hydrogen atoms are linked by 6 double bonds, and is usually contained in the human body and animal and vegetable fats and oils. Squalene has been used for various uses in the industries, such as an acid-fast functional supplement food, a cosmetic raw material, a vaccine support raw material, and a feed raw material. According to a report (Global Trends & Forecasts to 2019), the market of squalene is expected to grow to 177.06 million dollars, the average annual growth rate of the market is 10.3%, and the market tends to grow every year. Squalene has been generally obtained by extraction from the liver of deep-water sharks, but this method is against animal protection policies, and squalene may be also extracted from vegetables, but the method for extracting squalene from vegetables is inefficient because wide lands are required for cultivation. Recently, starting from yeast strains, various attempts such as a method for producing squalene from microalgae, and the like have been continued, and methods using yeast need a lot of sugars during the production process, and thus are economically inefficient, and when microalgae are used, the limitation thereof is clear because other impurities in addition to squalene, which is a desired target material, are produced. Therefore, there is a need for studies on a method which may economically and stably mass-produce squalene.

SUMMARY

In an aspect, an object of the present disclosure is to produce squalene by an eco-friendly method using microorganisms.

In another aspect, an object of the present disclosure is to provide a *Synechococcus elongatus* strain having a capability of producing squalene.

In still another aspect, an object of the present disclosure is to continuously mass-produce squalene using the *Synechococcus elongatus* strain.

In yet another aspect, an object of the present disclosure is to produce squalene using carbon dioxide to be discarded as a carbon source.

In an exemplary embodiment, the present disclosure provides a *Synechococcus elongatus* strain including: a gene encoding an enzyme producing 1-deoxy-D-xylulose 5-phosphate from pyruvate and D-glyceraldehyde 3-phosphate; a gene encoding an enzyme producing dimethylallyl diphosphate from isopentenyl diphosphate; a gene encoding an enzyme producing dimethylallyl diphosphate from isopentenyl diphosphate; a gene encoding an enzyme producing farnesyl diphosphate from dimethylallyl diphosphate; and a gene encoding an enzyme producing squalene from farnesyl diphosphate.

In another exemplary embodiment, the present disclosure provides a method for preparing squalene, the method including: culturing the strain.

In another exemplary embodiment, the present disclosure provides a method for removing carbon dioxide, the method including: culturing the strain.

In an aspect of the present disclosure, a transformed *Synechococcus elongatus* strain may mass-produce squalene using carbon dioxide as a carbon source. The *Synechococcus elongatus* strain is economically efficient because a high-value added squalene is produced using light and carbon dioxide present in the atmosphere as a carbon source, and the method for producing squalene is eco-friendly because the strain may be utilized to remove or reduce carbon dioxide in the atmosphere by using microorganisms. The strain of the present disclosure may produce only squalene, which is a desired target material with high purity, and has an advantage in that squalene may be continuously mass-produced.

BRIEF DESCRIPTION OF THE DRAWINGS

In FIGS. 3 and 5, WT means a wild-type strain, SeSC33S means a mutant strain of a *Synechococcus elongatus* strain, in which a pSe1Bb1s-dxs-idi-ispA vector at an NSI site and a pSe2Bb1k-sqs vector (including a squalene synthase gene derived from *Saccharomyces cerevisiae*) at an NSII site are transformed, and SeSC34S means a mutant strain of a *Synechococcus elongatus* strain, which is transformed with a pSe1Bb1s-dxs-idi-ispA vector at an NSI site and a pSe2Bb1k-sqs vector (including a squalene synthase gene derived from *Methylococcus capsulatus*) at an NSII site. Further, SeSC41S means a mutant strain of a *Synechococcus elongatus* strain, which is transformed with a pSe1Bb1s-dxs-dxr-idi-ispA vector at an NSI site and a pSe2Bb1k-sqs vector (including a squalene synthase gene derived from *Saccharomyces cerevisiae*) at an NSII site, and SeSC42S means a mutant strain of a *Synechococcus elongatus* strain, in which a pSe1Bb1s-dxs-dxr-idi-ispA vector at an NSI site and a pSe2Bb1k-sqs vector (including a squalene synthase gene derived from *Methylococcus capsulatus*) at an NSII site are transformed.

DETAILED DESCRIPTION

Figure 1:
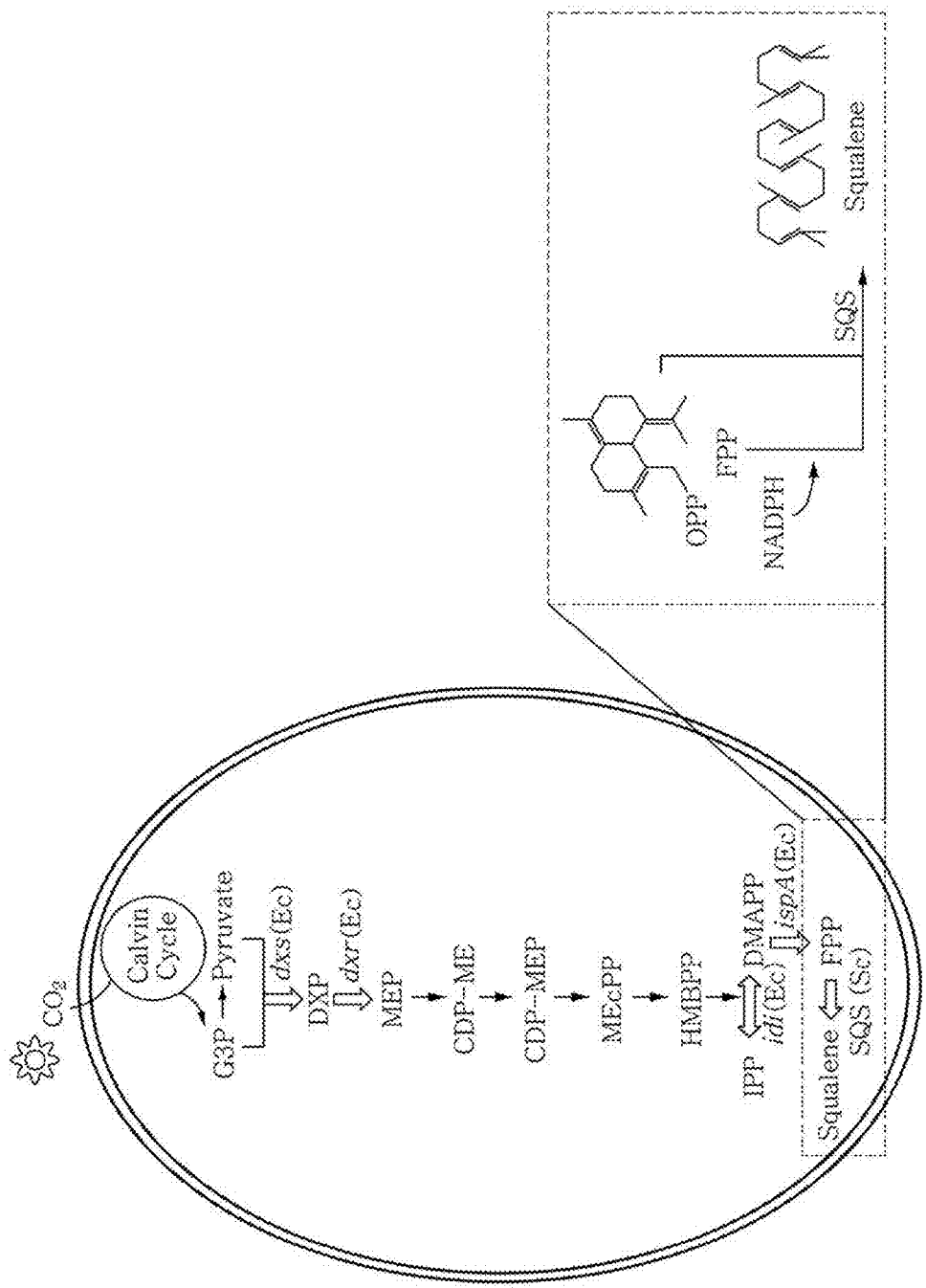
FIG. 1 is a view illustrating a production pathway for a transformed *Synechococcus elongatus* strain (CDP-ME is an acronym for 4-diphosphocytidyl-2-C-methyl-D-erythritol, CDP-MEP is an acronym for 4-diphosphocytidyl-2-C-methyl-D-erythritol-2-phosphate, ME-cPP is an acronym for 2-C-Methyl-D-erythritol-2,4-cyclopyrophosphate, and HMBPP is an acronym for 4-hydroxy-3-methyl-but-2-enyl pyrophosphate).

Cyanobacteria are microorganisms which may produce energy through photosynthesis and fix carbon dioxide to produce metabolites. Cyanobacteria being prokaryotes are easy to be genetically modified compared to microalgae being eukaryotes, and thus are advantageous for altering metabolic pathways or artificially regulating metabolites. Recently, various biofuel substitutes or chemical products have been produced by introducing a synthetic biological/metabolic engineering technique based on the genetic modification technology to use metabolic pathways that have not existed.

The present inventors genetically modified a *Synechococcus elongatus* strain, one of cyanobacteria, thereby constructing a new mutant strain which may directly produce a squalene material from carbon dioxide.

Hereinafter, the present disclosure will be described in detail.

In an aspect, the present disclosure is a *Synechococcus elongatus* strain including: a gene encoding an enzyme producing 1-deoxy-D-xylulose 5-phosphate (DXP) from pyruvate and D-glyceraldehyde 3-phosphate (G3P); a gene encoding an enzyme producing dimethylallyl diphosphate (DMAPP) from isopentenyl diphosphate (IPP); a gene encoding an enzyme producing farnesyl diphosphate (FPP) from dimethylallyl diphosphate (DMAPP); and a gene encoding an enzyme producing squalene from farnesyl diphosphate (FPP).

The gene encoding the enzyme producing 1-deoxy-D-xylulose 5-phosphate (DXP) from pyruvate and D-glyceraldehyde 3-phosphate (G3P) may be a deoxyxylulose-5-phosphate synthase. Further, the gene encoding the enzyme producing dimethylallyl diphosphate (DMAPP) from isopentenyl diphosphate (IPP) may be an isopentenyl diphosphate delta isomerase. In addition, the enzyme producing farnesyl diphosphate (FPP) from dimethylallyl diphosphate (DMAPP) may be a geranyl diphosphate synthase, and the enzyme producing squalene from farnesyl diphosphate (FPP) may be a squalene synthase.

The strain may mass-produce farnesyl diphosphate (FPP) which is a precursor of squalene, and thus may mass-produce squalene therefrom. The strain may synthesize squalene from two molecules of farnesyl diphosphate.

For example, the gene encoding the enzyme producing 1-deoxy-D-xylulose 5-phosphate (DXP) from pyruvate and D-glyceraldehyde 3-phosphate (G3P) may be derived from *E. coli*. Furthermore, the gene encoding the enzyme producing dimethylallyl diphosphate (DMAPP) from isopentenyl diphosphate (IPP) may be derived from *E. coli*, and the gene encoding the enzyme producing farnesyl diphosphate (FPP) from dimethylallyl diphosphate (DMAPP) may also be derived from *E. coli*. Meanwhile, the gene encoding the enzyme producing squalene from farnesyl diphosphate (FPP) may be derived from *Saccharomyces cerevisiae* or may be derived from *Methylococcus capsulatus*.

In an exemplary embodiment, the gene encoding the enzyme producing 1-deoxy-D-xylulose 5-phosphate (DXP) from pyruvate and D-glyceraldehyde 3-phosphate (G3P) may include a sequence of SEQ ID NO. 1.

Further, the gene encoding the enzyme producing dimethylallyl diphosphate (DMAPP) from isopentenyl diphosphate (IPP) may include a sequence of SEQ ID NO. 2. In addition, in an exemplary embodiment, the gene encoding the enzyme producing farnesyl diphosphate (FPP) from dimethylallyl diphosphate (DMAPP) may include a sequence of SEQ ID NO. 3.

In an exemplary embodiment, the gene encoding an enzyme producing squalene from farnesyl diphosphate (FPP) may include a sequence of SEQ ID NO. 4 or 5. The sequence of SEQ ID NO. 4 includes a squalene synthase gene derived from *Saccharomyces cerevisiae*, and the sequence of SEQ ID NO. 5 includes a squalene synthase gene derived from *Methylococcus capsulatus*.

In an exemplary embodiment, the strain may further include a gene encoding an enzyme producing 2-C-methyl-D-erythritol-4-phosphate (MEP) from 1-deoxy-D-xylulose 5-phosphate (DXP). The gene encoding the enzyme producing 2-C-methyl-D-erythritol-4-phosphate (MEP) from 1-deoxy-D-xylulose 5-phosphate (DXP) may be derived from *E. coli*. The gene encoding the enzyme producing 2-C-methyl-D-erythritol-4-phosphate (MEP) from 1-deoxy-D-xylulose 5-phosphate (DXP) may be a 1-deoxy-D-xylulose-5-phosphate reductase. Meanwhile, in an exemplary embodiment, the gene encoding the enzyme producing 2-C-methyl-D-erythritol-4-phosphate (MEP) from 1-deoxy-D-xylulose 5-phosphate (DXP) may include a sequence of SEQ ID NO. 6.

In the present specification, the gene encoding an enzyme producing 1-deoxy-D-xylulose 5-phosphate (DXP) from pyruvate and D-glyceraldehyde 3-phosphate (G3P) is referred to as 'dxs gene'. Furthermore, in the present specification, the gene encoding the enzyme producing dimethylallyl diphosphate (DMAPP) from isopentenyl diphosphate (IPP) is referred to as 'idi gene', the gene encoding the enzyme producing farnesyl diphosphate (FPP) from dimethylallyl diphosphate (DMAPP) is referred to as 'ispA gene', the gene encoding the enzyme producing squalene from farnesyl diphosphate (FPP) is referred to as 'sqs gene', and the gene encoding the enzyme producing 2-C-methyl-D-erythritol-4-phosphate (MEP) from 1-deoxy-D-xylulose 5-phosphate (DXP) is also referred to as 'dxr gene'.

In an exemplary embodiment, the strain may be transformed with a first vector and/or a second vector. The expression 'the first or the second' is used only to differentiate the type of vector, and does not limit the order or method of transformation.

The first vector may include: the gene encoding the enzyme producing 1-deoxy-D-xylulose 5-phosphate (DXP) from pyruvate and D-glyceraldehyde 3-phosphate (G3P); the gene encoding the enzyme producing dimethylallyl diphosphate (DMAPP) from isopentenyl diphosphate (IPP); and the gene encoding the enzyme producing farnesyl diphosphate (FPP) from dimethylallyl diphosphate (DMAPP). The first vector may include a sequence of SEQ ID NO. 7.

Further, the first vector further include the gene encoding the enzyme producing 2-C-methyl-D-erythritol-4-phosphate (MEP) from 1-deoxy-D-xylulose 5-phosphate (DXP). The first vector may include a sequence of SEQ ID NO. 8.

In an exemplary embodiment, the strain may be transformed with only the first vector, and in this case, the strain mass-produces farnesyl diphosphate (FPP) which is a precursor of squalene, and thus may separately produce squalene by using the same.

In an exemplary embodiment, the second vector may include the gene encoding the enzyme producing squalene from farnesyl diphosphate (FPP). The second vector may include a sequence of SEQ ID NO. 9 or 10. A second vector including the sequence of SEQ ID NO. 9 includes a squalene synthase gene derived from *Saccharomyces cerevisiae*, and a second including the sequence of SEQ ID NO. 10 includes a squalene synthase gene derived from *Methylococcus capsulatus*.

The first vector may be inserted into a neutral site I (NSI) of *Synechococcus elongatus* which is a parent strain.

In addition, the second vector may be inserted into a neutral site II (NSII) of *Synechococcus elongatus* which is a parent strain.

The first vector may sequentially include: a spectinomycin-resistant gene as selection marker; a lacI repressor; a trc promoter; and a target gene. The target gene may be the gene encoding the enzyme producing 1-deoxy-D-xylulose 5-phosphate (DXP) from pyruvate and D-glyceraldehyde 3-phosphate (G3P); the gene encoding the enzyme producing dimethylallyl diphosphate (DMAPP) from isopentenyl diphosphate (IPP); and the gene encoding the enzyme producing farnesyl diphosphate (FPP) from dimethylallyl diphosphate (DMAPP). The first vector may include a sequence of SEQ ID NO. 7.

Furthermore, the first vector may further include the gene encoding the enzyme producing 2-C-methyl-D-erythritol-4-phosphate (MEP) from 1-deoxy-D-xylulose 5-phosphate (DXP) as the target gene. The first vector further including the gene encoding the enzyme producing 2-C-methyl-D-erythritol-4-phosphate (MEP) from 1-deoxy-D-xylulose 5-phosphate (DXP) may include a sequence of SEQ ID NO. 8.

The target genes to be inserted into the first vector may be each derived from *E. coli*.

In the present specification, the target gene may mean a gene which is expressed in a strain and inserted into a vector so as to exhibit the function of the corresponding gene.

The second vector may sequentially include: a kanamycin-resistant gene as selection marker;

a lacI repressor; a trc promoter; and a target gene. The target gene may be a gene encoding an enzyme producing squalene from farnesyl diphosphate (FPP). The gene encoding the enzyme producing squalene from farnesyl diphosphate (FPP) may be derived from *Saccharomyces cerevisiae* or *Methylococcus capsulatus*. The second vector may include a sequence of SEQ ID NO. 9 or 10.

The target genes to be inserted into the first vector and the second vector may be located between the BglII site and the BamHI site, which are restriction enzyme sites.

In the vector disclosed in the present specification, all the genes are linked operably to each other. The term "operably" means that the target genes may be expressed normally.

The strain may be a strain in which the first vector and/or the second vector are/is transformed with *Synechococcus elongatus* PCC7942 (Accession number: ATCC 33912), which is a parent strain. Into the parent strain, only the first vector may be introduced, and both the first vector and the second vector may also be introduced.

The strain may be a strain belonging to accession number KCTC 12966BP. The accession number KCTC 12966BP strain may mean a strain of a *Synechococcus elongatus* strain, in which a pSe1Bb1s-dxs-idi-ispA vector at an NSI site and a pSe2Bb1k-sqs vector (including a squalene synthase gene derived from *Saccharomyces cerevisiae*) at an NSII site are transformed.

In another aspect, the present disclosure is a method for producing squalene, the method including: culturing the transformed *Synechococcus elongatus* strain.

The culturing may be performed under conditions of 0.1% to 10% $CO_2$ and a temperature of 10° C. to 40° C. For example, the strain may be cultured under conditions of a 5% $CO_2$ concentration and 30° C.

Further, In another aspect, the present disclosure is a method for removing carbon dioxide, the method including: culturing the transformed *Synechococcus elongatus* strain.

EXAMPLES

Hereinafter, the present disclosure will be described in more detail through the Examples. However, the following Examples are provided only for illustrative purposes to facilitate the understanding of the present disclosure, and the purview and scope of the present disclosure is not limited thereto.

Example 1

Referring to a prior paper (Kim, S. W., Keasling, J. D., 2001. Metabolic engineering of the nonmevalonate isopentenyl diphosphate synthesis pathway in *Escherichia coli* enhances lycopene production. Biotechnol. Bioeng. 72, 408-415), a methylerythritol phosphate pathway (MEP pathway) and a metabolic pathway from pyruvic acid and D-glyceraldehyde 3-phosphate to farnesyl diphosphate were newly created. The DNA sequences of dxs gene, dxr gene, idi gene, and ispA gene of *E. coli* was subjected to codon optimization, and then the sequences were custom synthesized and constructed from Genescript®.

Example 2 Construction of Four Squalene-Producing Strains Using SyneBrick Vectors pSe1Bb1s-GFP Vector and pSe2Bb1k-GFP Vector A first vector was constructed by using a pSe1Bb1s-GFP vector. The pSe1Bb1s-GFP vector was constructed by using a pBbE1c-RFP vector (Lee T S, Krupa R A, Zhang F, Hajimorad M, Holtz W J, Prasad N, Lee S K, Keasling J D (2011b) BglBrick vectors and datasheets: a synthetic biology platform for gene expression. J Biol Eng 5:12) and a pSeBb1k-GFP vector (Lee T S, Krupa R A, Zhang F, Hajimorad M, Holtz W J, Prasad N, Lee S K, Keasling J D (2011b) BglBrick vectors and datasheets: a synthetic biology platform for gene expression. J Biol Eng 5:12).

Figure 2A:
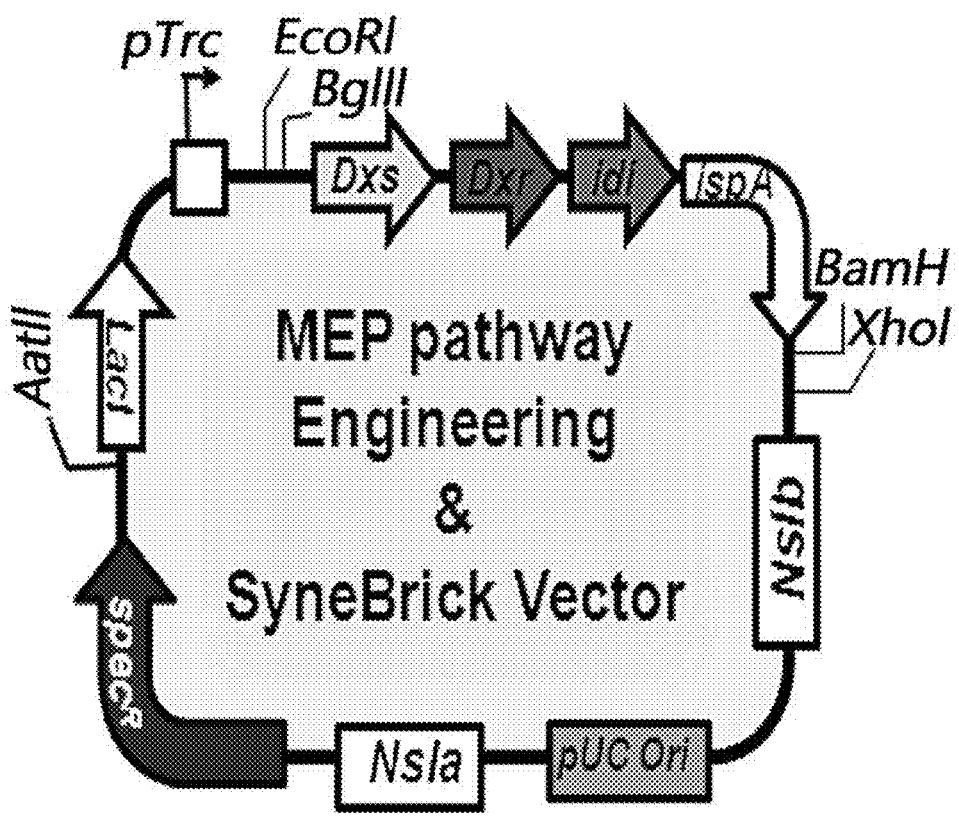
FIG. 2a is a schematic view of a first vector according to an exemplary embodiment.
Figure 2B:
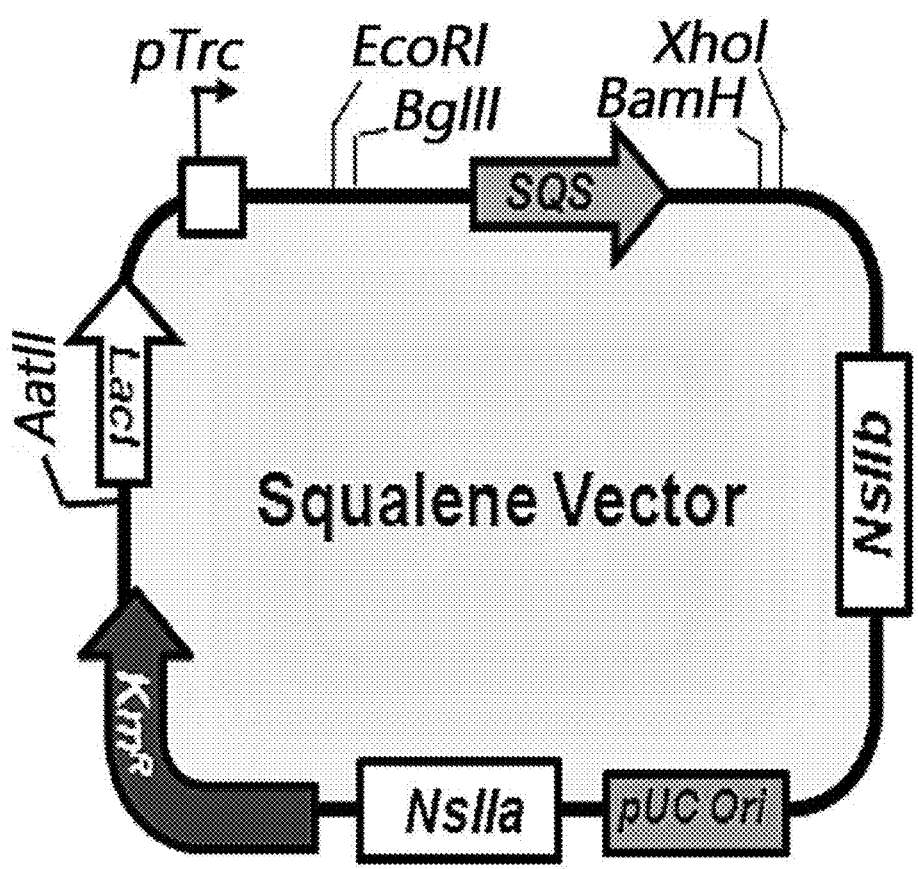
FIG. 2b is a schematic view of a second vector according to an exemplary embodiment.

The GFP portion of the SyneBrick vector pSe1Bb1s-GFP was removed by using the EcoRI-BglII restriction enzyme, and then a DNA sequence of the ispA gene treated with the custom synthesized EcoRI-BamHI restriction enzyme was inserted into the site. The pSe1Bb1s-ispA vector thus completed was treated with the EcoRI-BglII restriction enzyme, and then a DNA sequence of the idi gene treated with the EcoRI-BamHI restriction enzyme was inserted thereinto. In the same manner, the dxs gene or the dxs gene-dxr gene was sequentially inserted thereinto, thereby finally constructing 'pSe1Bb1s-dxs gene-idi gene-ispA gene' and 'pSe1Bb1s-dxs gene-dxr gene-idi gene-ispA gene' vectors (FIG. 2a). The completed vector was inserted into the Neutral Site-I of a wide-type S. elongatus PCC7942 strain. A transformed S. elongatus PCC7942 strain, in which the intermediate flow of the MEP metabolic pathway was increased, was constructed. Transformation was confirmed through PCR (5'→3' Primer Sequence: Forward: CCAGCAGCGGCTGCCTGC-CCAAAAG (SEQ ID NO. 11))/Reverse: GAAAGCGT-GACGAGCAGGGA (SEQ ID NO. 12). Meanwhile, the second vector was constructed by using pSe2Bb1k-GFP. Referring to the document information, the GFP portion of the SyneBrick vector pSe2Bb1k-GFP was removed by using the EcoRI-BamHI restriction enzyme, and then a custom synthesized DNA sequence of a squalene synthase gene of *Methylococcus capsulatus* or *Saccharomyces cerevisiae* was inserted thereinto. The completed pSe2Bb1k-sqs gene vector (FIG. 2b) was inserted into the Neutral Site-II of the transformed S. elongatus PCC7942 strain described above, in which the intermediate flow of the MEP metabolic pathway was increased. Transformation was confirmed through PCR (5'→3' Primer Sequence: Forward: GGC-TACGGTTCGTAATGCCA (SEQ ID NO. 13))/Reverse: GAGATCAGGGCTGTACTTAC (SEQ ID NO. 14).

Example 3 Confirmation of Transformed Strain's Capability of Producing Squalene

The transformed strains prepared in Example 2 were cultured for a predetermined time to test whether squalene was produced from 5% carbon dioxide which was directly supplied. As a specific culturing condition, 100 ml of a BG-11 medium including a 10 mM MOPS buffer was put into a 100 ml-bottle, the constructed squalene producing strain was diluted at an O.D of 0.6 when initially cultured, and the diluted solution was put into the medium. Further, 10 ug/ml of a spectinomycin antibiotic and 5 ug/ml of kanamycin were put into the medium, and then the resulting medium was cultured under conditions continuously supplying 100 uE m−2 s−1 and 5% $CO_2$ at 30° C. in a stationary incubator. An inducer 1 mM IPTG required for expression of genes was put into the medium 1 day after the initiation of culturing, the optical density of cells was measured at a wavelength of 730 nm until 8 days after culturing, and the amount of squalene produced was also measured during the culturing for 8 days.

Figure 3:
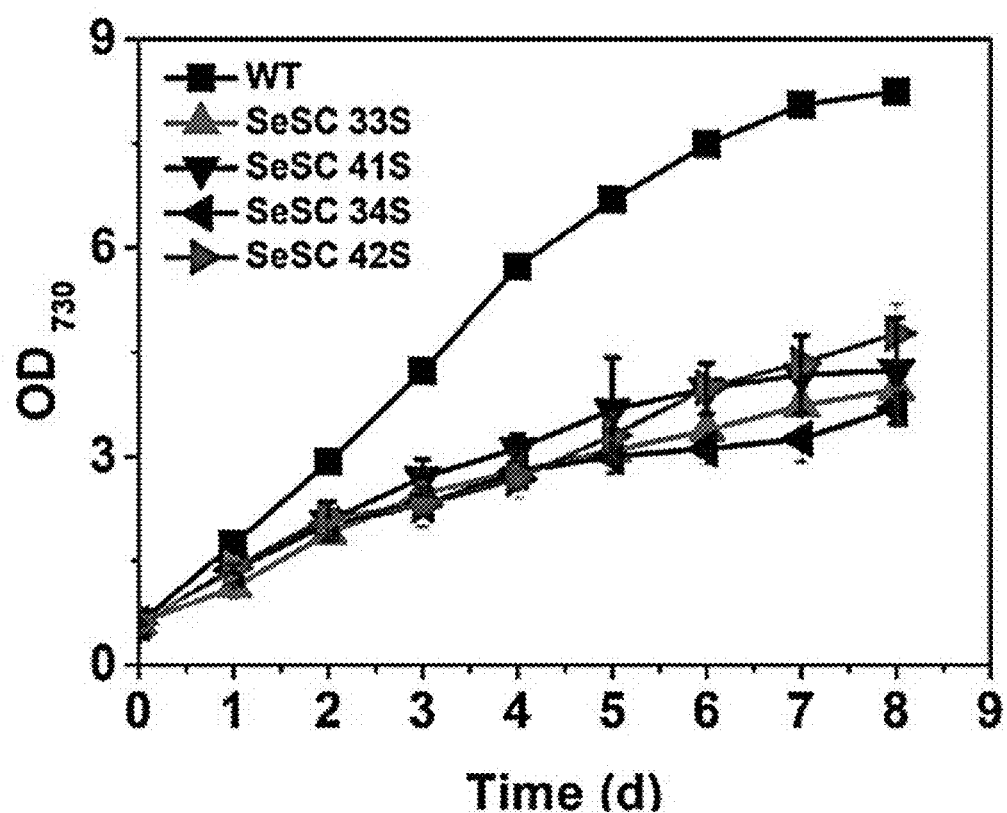
FIG. 3 is a view illustrating the growth of a wide-type strain and a transformed strain.
Figure 4A:
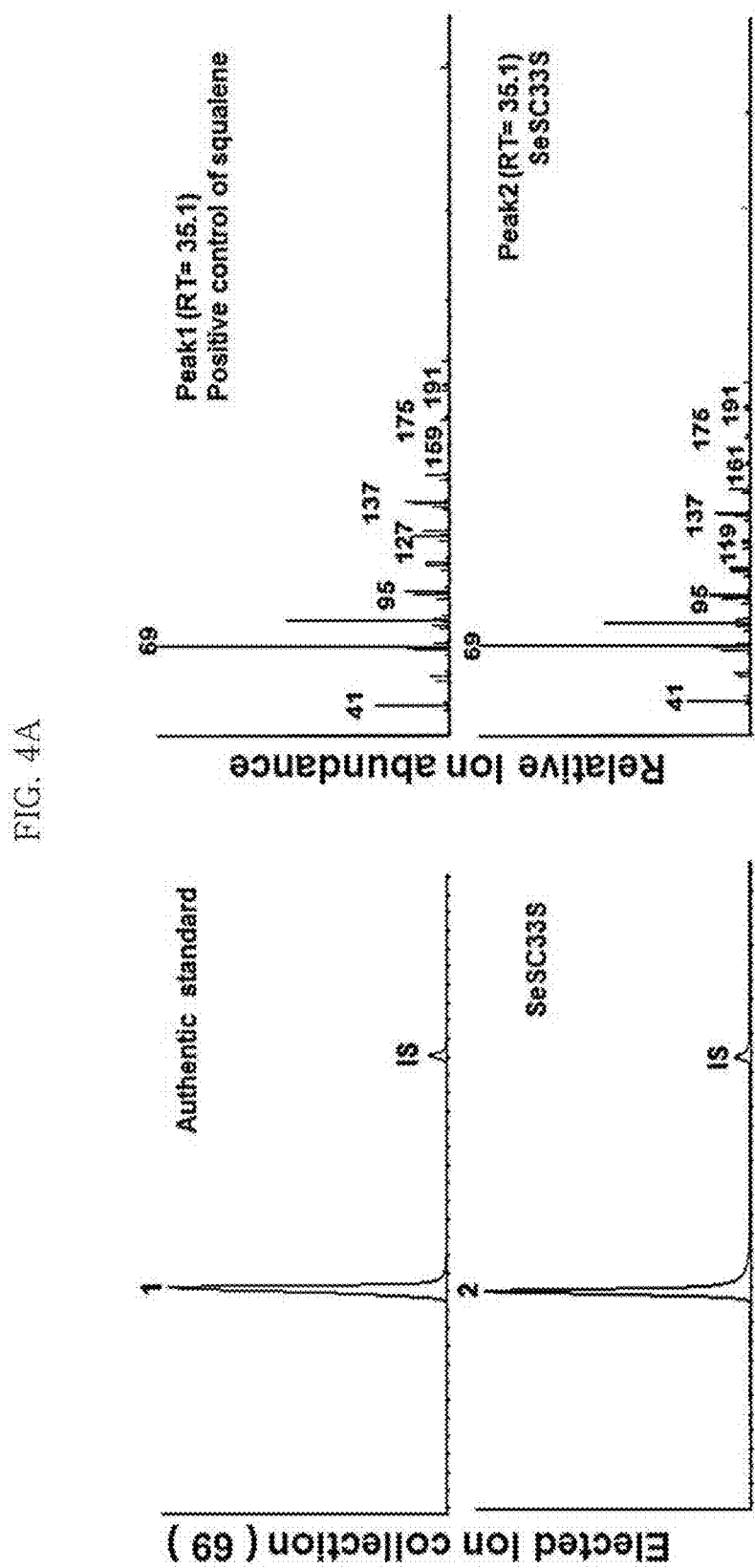
FIG. 4a is a view illustrating a gas chromatography result confirming that a material produced by the transformed strain is squalene.
Figure 4B:
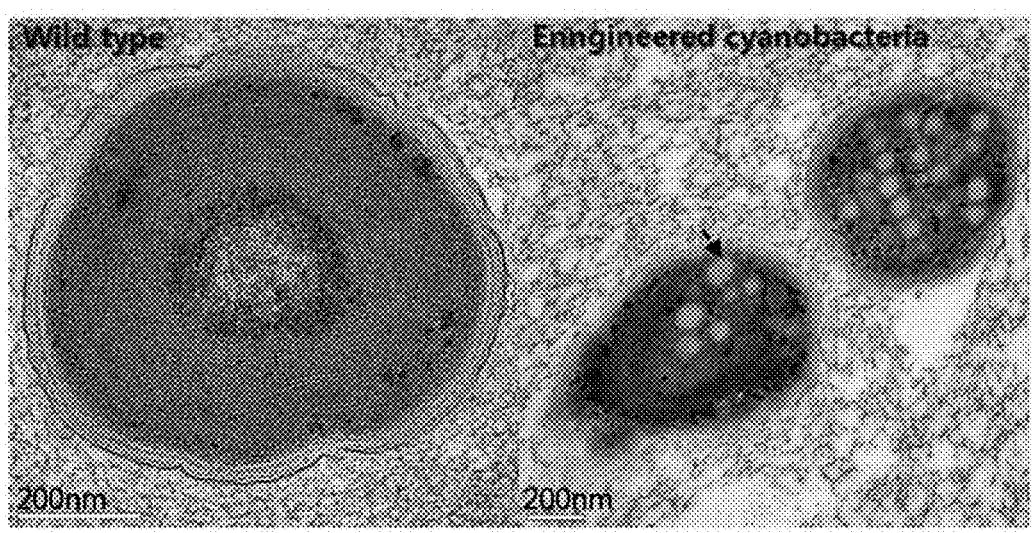
FIG. 4b is a photograph confirming squalene produced by the transformed strain by the unaided eye.
Figure 5:
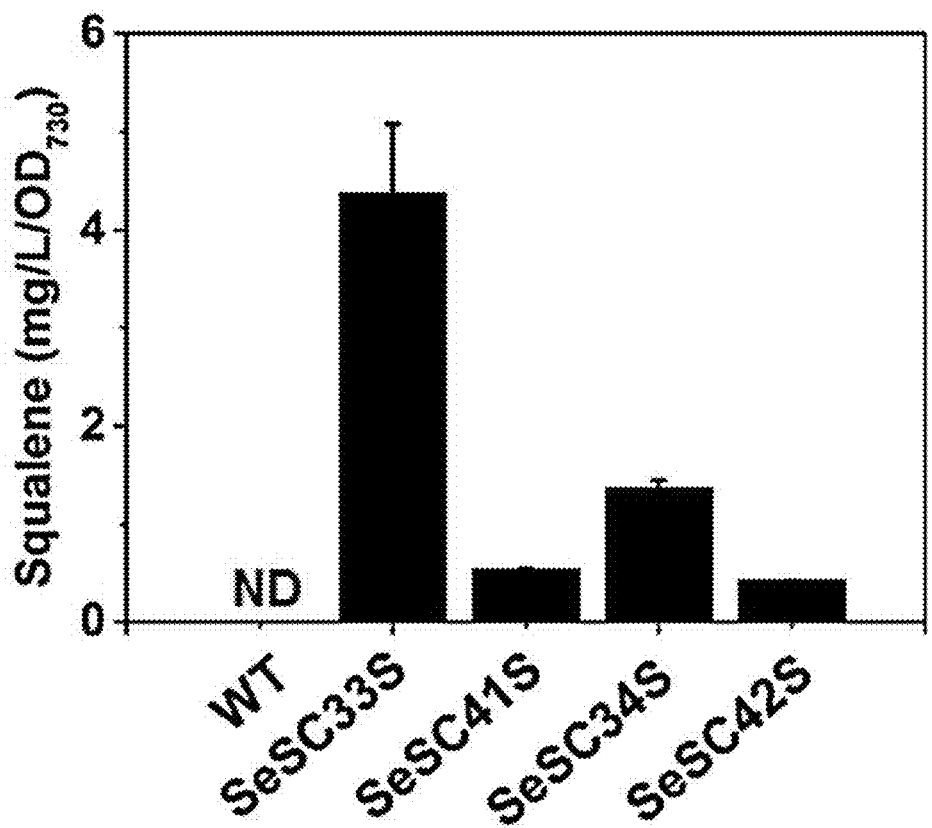
FIG. 5 is a view illustrating a result confirming that the transformed strain has a capability of producing squalene.

The growth curves of four transformed strains and the wild-type strain are as illustrated in FIG. 3. Further, through a gas chromatography analysis method, it was confirmed that the material produced from the strain was squalene (FIGS. 4a and 4b). The transformed strain into which 'pSe1Bb1k-dxs gene-dxr gene-idi gene-ispA gene' was inserted produced up to 0.41 to 0.12 mg/L/OD730 of squalene for the culture time. Moreover, the strain into which the pSe1Bb1k-dxs gene-idi gene-ispA gene was inserted produced up to 4.98 to 1.36 mg/L/OD730 of squalene for the culture time (FIG. 5).

ACCESSION NUMBER

Depositary Institution: Korea Research Institute of Bioscience & Biotechnology
Accession number: KCTC12966BP
Commissioned date: 2015 Dec. 18

What is claimed is:

1. A *Synechococcus elongatus* strain comprising:
    a gene encoding an enzyme producing 1-deoxy-D-xylulose 5-phosphate (DXP) from pyruvate and D-glyceraldehyde 3-phosphate (G3P) comprising a sequence of SEQ ID NO. 1;
    a gene encoding an enzyme producing dimethylallyl diphosphate (DMAPP) from isopentenyl diphosphate (IPP) comprising a sequence of SEQ ID NO. 2;
    a gene encoding an enzyme producing farnesyl diphosphate (FPP) from dimethylallyl diphosphate (DMAPP) comprising a sequence of SEQ ID NO. 3; and
    a gene encoding an enzyme producing squalene from farnesyl diphosphate (FPP) comprising a sequence of SEQ ID NO. 4 or 5.

2. The *Synechococcus elongatus* strain according to claim 1, wherein the enzyme producing 1-deoxy-D-xylulose 5-phosphate (DXP) from pyruvate and D-glyceraldehyde 3-phosphate (G3P) is a deoxyxylulose-5-phosphate synthase,
    the enzyme producing dimethylallyl diphosphate (DMAPP) from isopentenyl diphosphate (IPP) is an isopentenyl diphosphate delta isomerase,
    the enzyme producing farnesyl diphosphate (FPP) from dimethylallyl diphosphate (DMAPP) is a geranyl diphosphate synthase, and
    the enzyme producing squalene from farnesyl diphosphate (FPP) is a squalene synthase.

3. The *Synechococcus elongatus* strain according to claim 1, wherein the gene encoding the enzyme producing 1-deoxy-D-xylulose 5-phosphate (DXP) from pyruvate and D-glyceraldehyde 3-phosphate (G3P);
    the gene encoding the enzyme producing dimethylallyl diphosphate (DMAPP) from isopentenyl diphosphate (IPP); and
    the gene encoding the enzyme producing farnesyl diphosphate (FPP) from dimethylallyl diphosphate (DMAPP) are each derived from *E. coli*, and
    the gene encoding the enzyme producing squalene from farnesyl diphosphate (FPP) is derived from *Saccharomyces cerevisiae* or *Methylococcus capsulatus*.

4. The *Synechococcus elongatus* strain according to claim 1, wherein the strain is transformed with a first vector and a second vector,
    the first vector comprising:
    a gene encoding an enzyme producing 1-deoxy-D-xylulose 5-phosphate (DXP) from pyruvate and D-glyceraldehyde 3-phosphate (G3P);
    a gene encoding an enzyme producing dimethylallyl diphosphate (DMAPP) from isopentenyl diphosphate (IPP); and
    a gene encoding an enzyme producing farnesyl diphosphate (FPP) from dimethylallyl diphosphate (DMAPP), and
    the second vector comprising: a gene encoding an enzyme producing squalene from farnesyl diphosphate (FPP).

5. The *Synechococcus elongatus* strain according to claim 4, wherein the first vector comprises a sequence of SEQ ID NO. 7.

6. The *Synechococcus elongatus* strain according to claim 4, wherein the second vector comprises a sequence of SEQ ID NO. 9, or a sequence of SEQ ID NO. 10.

7. The *Synechococcus elongatus* strain according to claim 4, wherein the first vector is inserted into a neutral site I (NSI) of *Synechococcus elongatus* which is a parent strain, and the second vector is inserted into a neutral site II (NSII) of *Synechococcus elongatus* which is a parent strain.

8. The *Synechococcus elongatus* strain according to claim 4, wherein the first vector sequentially comprises:
- a spectinomycin-resistant gene;
- a lacI repressor;
- a trc promoter; and
- a target gene(s), and
- wherein the target genes are
  - the gene encoding the enzyme producing 1-deoxy-D-xylulose 5-phosphate (DXP) from pyruvate and D-glyceraldehyde 3-phosphate (G3P);
  - the gene encoding the enzyme producing dimethylallyl diphosphate (DMAPP) from isopentenyl diphosphate (IPP); and
  - the gene encoding the enzyme producing farnesyl diphosphate (FPP) from dimethylallyl diphosphate (DMAPP).

9. The *Synechococcus elongatus* strain according to claim 4, wherein the second vector sequentially comprises:
- a kanamycin-resistant gene;
- a lacI repressor;
- a trc promoter; and
- a target gene encoding the enzyme producing squalene from farnesyl diphosphate (FPP).

10. The *Synechococcus elongatus* strain according to claim 4, wherein the strain is a strain in which the vectors are transformed in *Synechococcus elongatus* PCC7942 (Accession number: ATCC 33912), which is a parent strain.

11. The *Synechococcus elongatus* strain according to claim 1, wherein the strain is a strain belonging to accession number KCTC 12966BP.

* * * * *